(12) United States Patent
Abels et al.

(10) Patent No.: US 9,877,805 B2
(45) Date of Patent: Jan. 30, 2018

(54) METHODS FOR SHAPING GREEN BODIES AND ARTICLES MADE BY SUCH METHODS

(71) Applicant: Ormco Corporation, Orange, CA (US)

(72) Inventors: Norbert Abels, Homburg (DE); Claus H. Backes, Saarbrücken (DE)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 15/044,686

(22) Filed: Feb. 16, 2016

(65) Prior Publication Data

US 2016/0157963 A1 Jun. 9, 2016

Related U.S. Application Data

(60) Continuation of application No. 14/495,389, filed on Sep. 24, 2014, now Pat. No. 9,539,064, which is a (Continued)

(51) Int. Cl.
*A61C 7/12* (2006.01)
*C04B 35/638* (2006.01)
(Continued)

(52) U.S. Cl.
CPC .................. *A61C 7/12* (2013.01); *A61C 7/14* (2013.01); *A61C 13/0022* (2013.01); *B28B 11/12* (2013.01); *B28B 17/0036* (2013.01); *B29C 35/0805* (2013.01); *C04B 35/634* (2013.01); *C04B 35/638* (2013.01); *B29C 2035/0838* (2013.01); *C04B 2235/602* (2013.01); *C04B 2235/6022* (2013.01); *C04B 2235/612* (2013.01); *C04B 2235/658* (2013.01); *Y10T 428/24893* (2015.01)

(58) Field of Classification Search
CPC ..................................................... C04B 35/634
USPC .................................................. 264/400, 482
See application file for complete search history.

(56) References Cited

U.S. PATENT DOCUMENTS 4,604,057 A * 8/1986 Viglietti ................... A61C 7/16
433/9
4,661,059 A * 4/1987 Kanno ..................... A61C 7/16
433/9

(Continued)

FOREIGN PATENT DOCUMENTS

EP 1033193 * 6/2000

OTHER PUBLICATIONS

U.S. Patent and Trademark Office, Non-final Office Action issued in U.S. Appl. No. 14/810,796, dated Nov. 7, 2017.

*Primary Examiner* — Nahida Sultana
(74) *Attorney, Agent, or Firm* — Wood Herron & Evans LLP

(57) ABSTRACT

A method of shaping a green body provides a shaped green body comprised of a plurality of sinterable particles and an organic binder. Such a method includes: (1) molding a mixture of sinterable particles and organic binder into the shape of an initial green body or intermediate, wherein the sinterable particles include at least one of metal particles or ceramic particles; and (2) shaping the green body intermediate with at least one of a stream of energy or a stream of matter, wherein the shaping yields a green body having a desired shape. The shaped green body can be sintered in order to provide a hardened body having substantially the shape of the shaped green body.

13 Claims, 9 Drawing Sheets

Related U.S. Application Data continuation of application No. 12/398,624, filed on Mar. 5, 2009, now Pat. No. 8,871,132, which is a division of application No. 11/193,571, filed on Jul. 29, 2005, now abandoned, and a continuation-in-part of application No. 11/193,239, filed on Jul. 29, 2005, now abandoned, which is a continuation-in-part of application No. 11/042,025, filed on Jan. 25, 2005, now abandoned.

(51) Int. Cl.
*B28B 11/12* (2006.01)
*B28B 17/00* (2006.01)
*C04B 35/634* (2006.01)
*A61C 7/14* (2006.01)
*A61C 13/00* (2006.01)
*B29C 35/08* (2006.01)

(56) References Cited

U.S. PATENT DOCUMENTS

| | | | | |
|---|---|---|---|---|
| 4,842,513 | A * | 6/1989 | Haarmann | A61C 7/12 433/8 |
| 4,957,554 | A * | 9/1990 | Mathers | C04B 35/195 106/35 |
| 4,968,459 | A * | 11/1990 | Sernetz | C04B 35/6455 264/1.21 |
| 5,215,693 | A * | 6/1993 | Lee | C04B 35/622 264/128 |
| 5,232,361 | A * | 8/1993 | Sachdeva | A61C 7/12 433/8 |
| 5,238,627 | A * | 8/1993 | Matsuhisa | B28B 1/24 264/328.2 |
| 5,242,298 | A * | 9/1993 | Sernetz | C04B 35/115 264/1.21 |
| 5,267,854 | A * | 12/1993 | Schmitt | A61C 7/16 433/8 |
| 5,267,855 | A * | 12/1993 | Tuneberg | A61C 7/16 433/9 |
| 5,326,259 | A * | 7/1994 | Rohlcke | A61C 7/12 433/8 |
| 5,393,486 | A * | 2/1995 | Eckert | B22C 7/02 164/246 |
| 5,522,725 | A * | 6/1996 | Jordan | A61C 7/12 433/8 |
| 5,556,276 | A * | 9/1996 | Roman | A61B 90/94 433/23 |
| 5,589,430 | A * | 12/1996 | Krahn | C04B 35/111 501/120 |
| 5,595,484 | A * | 1/1997 | Orikasa | A61B 90/94 433/10 |
| 5,613,182 | A * | 3/1997 | Lynn | B22F 5/003 419/28 |
| 5,613,849 | A * | 3/1997 | Tanaka | A61L 27/06 420/417 |
| 5,616,026 | A * | 4/1997 | Cash | A61C 7/14 433/8 |
| 5,618,175 | A * | 4/1997 | Reher | A61C 7/141 433/16 |
| 5,622,494 | A * | 4/1997 | Andreiko | A61C 7/141 433/9 |
| 5,639,402 | A * | 6/1997 | Barlow | A61F 2/28 264/430 |
| 5,641,920 | A * | 6/1997 | Hens | B22F 1/0059 419/36 |
| 5,678,162 | A * | 10/1997 | Barlow | B22F 3/225 264/219 |
| 5,692,898 | A * | 12/1997 | Orikasa | A61B 90/94 433/8 |
| 5,730,928 | A * | 3/1998 | Ghosh | C04B 35/119 264/629 |
| 5,773,099 | A * | 6/1998 | Tanaka | A61L 27/06 264/16 |
| RE35,863 | E * | 7/1998 | Sachdeva | A61C 7/12 433/8 |
| 5,800,162 | A * | 9/1998 | Shimodaira | A61C 7/14 433/8 |
| 5,803,728 | A * | 9/1998 | Orikasa | A61B 90/94 433/8 |
| 5,829,973 | A * | 11/1998 | Andreiko | A61C 7/16 433/8 |
| 5,910,273 | A * | 6/1999 | Thiel | A61C 13/0003 264/16 |
| 5,911,102 | A * | 6/1999 | Takahashi | B22F 3/10 419/38 |
| 5,944,517 | A * | 8/1999 | Binder | A61C 7/16 433/23 |
| 5,948,342 | A * | 9/1999 | Nakazawa | B29C 67/0077 264/113 |
| 5,950,063 | A * | 9/1999 | Hens | B22F 1/0059 419/36 |
| 5,972,269 | A * | 10/1999 | Barros | B22D 17/24 264/221 |
| 6,027,686 | A * | 2/2000 | Takahashi | B22F 3/10 419/2 |
| 6,048,954 | A * | 4/2000 | Barlow | B29C 41/003 526/328.5 |
| 6,059,949 | A * | 5/2000 | Gal-Or | A61C 5/10 204/484 |
| 6,071,117 | A * | 6/2000 | Andreiko | A61C 7/16 433/9 |
| 6,095,809 | A * | 8/2000 | Kelly | A61C 7/20 433/20 |
| 6,155,331 | A * | 12/2000 | Langer | B22C 1/00 164/15 |
| 6,183,515 | B1 * | 2/2001 | Barlow | A61F 2/28 264/497 |
| 6,244,870 | B1 * | 6/2001 | Sakata | A61C 8/0048 106/38.22 |
| 6,276,930 | B1 * | 8/2001 | Pozzi | A61B 90/94 433/9 |
| 6,354,836 | B1 * | 3/2002 | Panzera | A61C 13/0006 433/215 |
| 6,391,251 | B1 * | 5/2002 | Keicher | B05B 7/14 419/7 |
| 6,444,167 | B1 * | 9/2002 | Shimodaira | A61C 7/16 419/37 |
| 6,495,073 | B2 * | 12/2002 | Bodenmiller | A61C 13/0003 264/16 |
| 6,495,794 | B2 * | 12/2002 | Shi | B29C 33/3842 219/121.67 |
| 6,521,004 | B1 * | 2/2003 | Culler | B24D 3/14 23/313 R |
| 6,531,678 | B2 * | 3/2003 | Yamamoto | B23K 26/067 219/121.71 |
| 6,537,487 | B1 * | 3/2003 | Kuhns | B21K 1/463 419/29 |
| 6,540,784 | B2 * | 4/2003 | Barlow | A61F 2/28 623/16.11 |
| 6,607,386 | B1 * | 8/2003 | Andersson | A61C 5/10 433/201.1 |
| 6,620,214 | B2 * | 9/2003 | McArdle | B24D 3/14 23/313 R |
| 6,627,835 | B1 * | 9/2003 | Chung | B23H 7/02 219/121.72 |
| 6,638,886 | B1 * | 10/2003 | Gupta | C23C 16/44 501/127 |
| 6,676,895 | B2 * | 1/2004 | Kuhns | B21K 1/463 419/36 |
| 6,710,290 | B2 * | 3/2004 | Yamamoto | B23K 26/067 219/121.71 |
| 6,733,703 | B2 * | 5/2004 | Billiet | B22F 1/0059 257/E21.504 |
| 6,739,959 | B2 * | 5/2004 | Bodenmiller | A61C 13/0003 451/364 |
| 6,744,618 | B2 * | 6/2004 | Divakar | H01L 21/6833 361/233 |

(56) References Cited

U.S. PATENT DOCUMENTS

| | | | |
|---|---|---|---|
| 6,811,744 B2* | 11/2004 | Keicher | B05B 7/14 264/112 |
| 6,814,926 B2* | 11/2004 | Geving | C22C 33/02 419/10 |
| 6,827,988 B2* | 12/2004 | Krause | C04B 33/24 427/596 |
| 6,846,862 B2* | 1/2005 | Schofalvi | B22F 1/0059 524/195 |
| 6,878,456 B2* | 4/2005 | Castro | A61K 6/0255 264/604 |
| 6,881,483 B2* | 4/2005 | McArdle | B24D 3/04 428/403 |
| 6,974,323 B2* | 12/2005 | Weigl | A61C 13/0004 219/121.72 |
| 6,984,261 B2* | 1/2006 | Cummings | A61K 6/0276 106/35 |
| 6,988,889 B2* | 1/2006 | Abels | A61C 7/00 433/24 |
| 6,994,549 B2* | 2/2006 | Brodkin | A61C 13/0003 264/19 |
| 7,011,522 B2* | 3/2006 | Panzera | A61C 13/0006 433/215 |
| 7,022,173 B2* | 4/2006 | Cummings | A61K 6/0276 106/35 |
| 7,045,237 B2* | 5/2006 | Sridhar | H01M 8/04022 429/465 |
| 7,063,813 B1* | 6/2006 | Nagaya | H01L 41/273 156/89.12 |
| 7,086,151 B2* | 8/2006 | Scancarello | B22F 3/225 29/527.1 |
| 7,125,248 B2* | 10/2006 | Phan | A61C 7/00 433/24 |
| 7,140,113 B2* | 11/2006 | King | B26B 21/58 30/346.54 |
| 7,162,321 B2* | 1/2007 | Luthardt | A61C 13/0004 264/16 |
| 7,236,842 B2* | 6/2007 | Kopelman | A61C 13/0004 433/218 |
| 7,300,488 B2* | 11/2007 | Szabo | C22C 1/0433 419/11 |
| 7,563,397 B2 | 7/2009 | Schulman et al. | |
| 7,563,608 B2* | 7/2009 | Ishikawa | C04B 35/447 435/176 |
| 2001/0043452 A1* | 11/2001 | Divakar | H01L 21/6833 361/234 |
| 2002/0033548 A1* | 3/2002 | Brodkin | A61C 13/0003 264/19 |
| 2002/0131886 A1* | 9/2002 | Kuhns | B21K 1/463 419/36 |
| 2002/0187065 A1* | 12/2002 | Amaya | B22F 3/225 419/8 |
| 2002/0187458 A1* | 12/2002 | Dolabdjian | A61C 13/0003 433/218 |
| 2003/0001313 A1* | 1/2003 | Krause | C04B 33/24 264/434 |
| 2003/0069638 A1* | 4/2003 | Barlow | A61F 2/28 623/16.11 |
| 2003/0125189 A1* | 7/2003 | Castro | A61K 6/0255 501/127 |
| 2003/0220424 A1* | 11/2003 | Schofalvi | B22F 1/0059 524/195 |
| 2004/0011453 A1* | 1/2004 | Roosen | B32B 18/00 156/89.11 |
| 2004/0048223 A1* | 3/2004 | Phan | A61C 7/00 433/24 |
| 2004/0081573 A1* | 4/2004 | Newell | B22F 1/0003 419/10 |
| 2004/0106087 A1* | 6/2004 | Weigl | A61C 13/0004 433/218 |
| 2004/0113301 A1* | 6/2004 | Burger | A61C 13/0003 264/16 |
| 2004/0118158 A1* | 6/2004 | Schwertfeger | C03B 19/06 65/33.2 |
| 2004/0119180 A1* | 6/2004 | Frank | A61C 13/0003 264/16 |
| 2004/0146423 A1* | 7/2004 | Scancarello | B22F 3/225 419/11 |
| 2004/0152034 A1* | 8/2004 | Cummings | A61K 6/0276 433/8 |
| 2004/0163262 A1* | 8/2004 | King | B26B 21/58 30/346.53 |
| 2004/0168610 A1* | 9/2004 | Conrad | C04B 35/46 106/35 |
| 2004/0182202 A1* | 9/2004 | Geving | C22C 33/02 75/252 |
| 2004/0188158 A1* | 9/2004 | Gebreselassie | B60R 13/083 180/89.1 |
| 2004/0226405 A1* | 11/2004 | Geving | C22C 33/02 75/252 |
| 2004/0234407 A1* | 11/2004 | Szabo | C22C 1/0433 419/14 |
| 2005/0023710 A1* | 2/2005 | Brodkin | A61C 13/0003 264/16 |
| 2005/0056350 A1* | 3/2005 | Dolabdjian | A61C 13/0003 148/512 |
| 2005/0109060 A1* | 5/2005 | Cummings | A61K 6/0276 65/17.6 |
| 2005/0133527 A1* | 6/2005 | Dullea | B05B 7/14 222/1 |
| 2005/0136176 A1* | 6/2005 | Rosenflanz | A61K 6/0276 427/2.1 |
| 2005/0196312 A1* | 9/2005 | Nyberg | B22F 1/0059 419/36 |
| 2005/0244782 A1* | 11/2005 | Chishti | A61C 7/00 433/24 |
| 2005/0261795 A1* | 11/2005 | Ghosh | A61C 13/0004 700/118 |
| 2006/0003095 A1* | 1/2006 | Bullen | B22F 3/004 427/180 |
| 2006/0150406 A1* | 7/2006 | Scancarello | B22F 3/225 29/888.022 |
| 2006/0166159 A1* | 7/2006 | Abels | A61C 7/14 433/8 |
| 2006/0168815 A1* | 8/2006 | Saliger | A61C 13/0022 29/896.11 |
| 2006/0185170 A1* | 8/2006 | Lewis | A61C 5/023 29/896.11 |
| 2006/0210781 A1* | 9/2006 | Nagaya | H01L 41/273 428/210 |
| 2006/0213602 A1* | 9/2006 | Yoshida | H01G 4/12 156/89.12 |
| 2006/0246397 A1* | 11/2006 | Wolf | A61C 8/0006 433/173 |
| 2007/0065329 A1* | 3/2007 | Nyberg | B22F 1/0059 419/60 |
| 2007/0068340 A1* | 3/2007 | Nyberg | B22F 1/0059 75/252 |
| 2007/0142206 A1* | 6/2007 | Binder | C04B 35/481 501/103 |
| 2007/0157475 A1* | 7/2007 | King | B26B 21/58 30/346.54 |
| 2007/0160949 A1* | 7/2007 | Voudouris | A61C 7/28 433/8 |
| 2007/0233299 A1* | 10/2007 | Kopelman | A61C 13/0004 700/98 |
| 2007/0264606 A1* | 11/2007 | Muha | A61C 7/28 433/17 |
| 2008/0057475 A1* | 3/2008 | Feith | A61C 8/0006 433/173 |
| 2008/0070182 A1* | 3/2008 | Wyllie | A61C 7/141 433/8 |
| 2008/0135305 A1* | 6/2008 | Smith | C22C 1/1036 175/374 |
| 2008/0202814 A1* | 8/2008 | Lyons | E21B 10/50 175/61 |
| 2008/0213718 A1* | 9/2008 | Abels | A61C 7/14 433/8 |

(56) References Cited

U.S. PATENT DOCUMENTS

| | | | |
|---|---|---|---|
| 2008/0223622 A1* | 9/2008 | Duggan | E21B 10/55 175/432 |
| 2009/0017411 A1* | 1/2009 | Pospisil | A61C 7/28 433/9 |
| 2012/0153549 A1* | 6/2012 | Milagres Ferri | B22F 3/1025 264/645 |
| 2014/0272800 A1* | 9/2014 | Howe | A61C 13/0004 433/199.1 |
| 2017/0087630 A1* | 3/2017 | Lee | B22D 25/02 |
| 2017/0141163 A1* | 5/2017 | Xiong | G09G 3/3258 |

* cited by examiner

METHODS FOR SHAPING GREEN BODIES AND ARTICLES MADE BY SUCH METHODS

CROSS-REFERENCE TO RELATED APPLICATIONS

This application is a continuation of U.S. patent application Ser. No. 14/495,389, filed Sep. 24, 2014, which is a continuation of U.S. patent application Ser. No. 12/398,624, filed on Mar. 5, 2009, which is a divisional of U.S. patent application Ser. No. 11/193,571, filed on Jul. 29, 2005, and is also a continuation-in-part of U.S. patent application Ser. No. 11/193,239, filed on Jul. 29, 2005, which is a continuation-in-part of U.S. patent application Ser. No. 11/042,025, filed on Jan. 25, 2005, and entitled "LASER SHAPING OF GREEN METAL BODY TO YIELD AN ORTHODONTIC BRACKET," with Norbert Abels and Claus H. Backes as inventors. The disclosures of the foregoing applications are incorporated by reference herein in their entirety.

TECHNICAL FIELD

The present invention relates to processes for manufacturing green bodies and sintered articles. More particularly, the present invention relates to cutting and shaping a green body intermediate with a stream of energy and/or matter prior to sintering so as to fabricate a green body having substantially the shape of the sintered article.

BACKGROUND

Traditionally, when tools, machinery parts, or other metal or ceramic components were designed and prepared for manufacturing, an extensive process of designing, fabricating, and retooling resulted in an extremely complicated and time consuming endeavor. The sequential iterations required to produce a metal or ceramic article with the proper dimensions and characteristics has become a significant and costly issue, especially considering the complexity of some of the more recently developed articles of manufacture. In part, the long lead times and high costs associated with research and development, when combined with the number of iterative production steps needed for perfecting a metal or ceramic article, has increased the time-to-market and associated costs. This has resulted in delayed profits for many manufacturers, and consequently, foregoing development of products that require costly prototypes.

In response, research and development has been driven to produce rapid prototyping and manufacturing technologies. As such, the development of rapid prototyping techniques has been provided the ability to design and retool prototypes in a much shorter time frame. In part, computer aided design and the ability to generate accurate three-dimensional computer images of the prototypes, sometimes by scanning a physical mockup, has enabled the iterative process to manipulate virtual images rather than the physical mockups.

Also, rapid prototyping has resulted in rapid tooling, which is an indirect method for producing working models from molds generated by the rapid prototyping process. As such, virtual objects can be precisely designed by manipulating computer images, which then are used for fabricating a physical mold before actually preparing the physical object. The physical objects prepared by these processes can then be tested to determine whether or not any one object will function for the desired use.

Additionally, these prototyping techniques have resulted in rapid manufacturing systems. These rapid manufacturing systems have integrated the computer aided prototyping capabilities with computer aided fabrication techniques such as stereolithography. Other rapid manufacturing techniques include jet solidification, three-dimensional welding, shape-deposition manufacturing, and laser-based manufacturing systems. The prevalent laser-based fabrication technologies include selective laser sintering, direct metal laser sintering, and laser engineered net shaping.

Briefly, these laser-based fabrication technologies build a prototype layer-by-layer using lasers to sinter or cure metal or ceramic powders one layer at a time until the article is finished. Moreover, additional sintering and metal infiltration steps may be required to produce a working piece. On the other hand, these laser-based fabrication technologies can be inadequate for preparing complex articles with protruding, overhanging, or other features that would be difficult to prepare one layer at a time. Additionally, these techniques are generally inadequate for manufacturing a high volume of end use articles. Thus, there still remains a need for improvements in rapid manufacturing processes to produce highly accurate prototypes as well as end use articles.

Therefore, it would be advantageous to have a fabrication technique for producing and shaping a metal or ceramic article without cutting or milling a hardened metal or ceramic material. Also, it would be beneficial to forego fabrication processes that require a prototype or working article to be manufactured one layer at a time.

SUMMARY

Generally, an embodiment of a method for shaping a green body can provide a green body having a desired shape that is substantially the shape of a sintered article prepared therefrom. Such a method includes molding a mixture of sinterable particles and organic binder into the shape of an initial green body. Additionally, the method includes further shaping the initial green body with a stream of energy and/or matter in order to obtain a shaped green body having a desired shape. To facilitate further shaping, the initial green body intermediate is comprised of a plurality of sinterable particles and an organic binder in an amount and distribution sufficiently holding the plurality of sinterable particles together so as to be form-stable while removing sinterable particles during shaping. The shaped green body is characterized as having at least one "stream-cut surface" thereon.

In another embodiment, a method of manufacturing can provide an article of manufacture comprised of a sintered body. Such a method includes molding a mixture of sinterable particles and organic binder into the shape of an initial green body intermediate. Also, shaping the initial green body intermediate with a stream of energy and/or matter results in a green body having a desired shape, wherein the desired shape is substantially the shape of the final sintered article. Additionally, sintering the shaped green body can be performed to yield an article having the desired shape.

Another embodiment includes an initial green body for use in preparing a stream-shaped green body. The initial green body is comprised of a plurality of sinterable particles, wherein the sinterable particles include at least one of a metal material or a ceramic material. Additionally, the green body is comprised of an organic binder matrix, wherein the organic binder at least partially coats each sinterable particle within the plurality of sinterable particles. The organic binder is characterized as having a thickness around a portion of the plurality of sinterable particles that separates one sinterable particle from another sinterable particle;

being sufficiently adhesive to hold the plurality of sinterable particles together; and forming a form-stable body in which the plurality of sinterable particles are initially bound together by the binder, wherein the form-stable body is capable of being shaped with at least one of a stream of energy or stream of matter while remaining form-stable in areas not subjected to the stream removal process.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Figure 1:
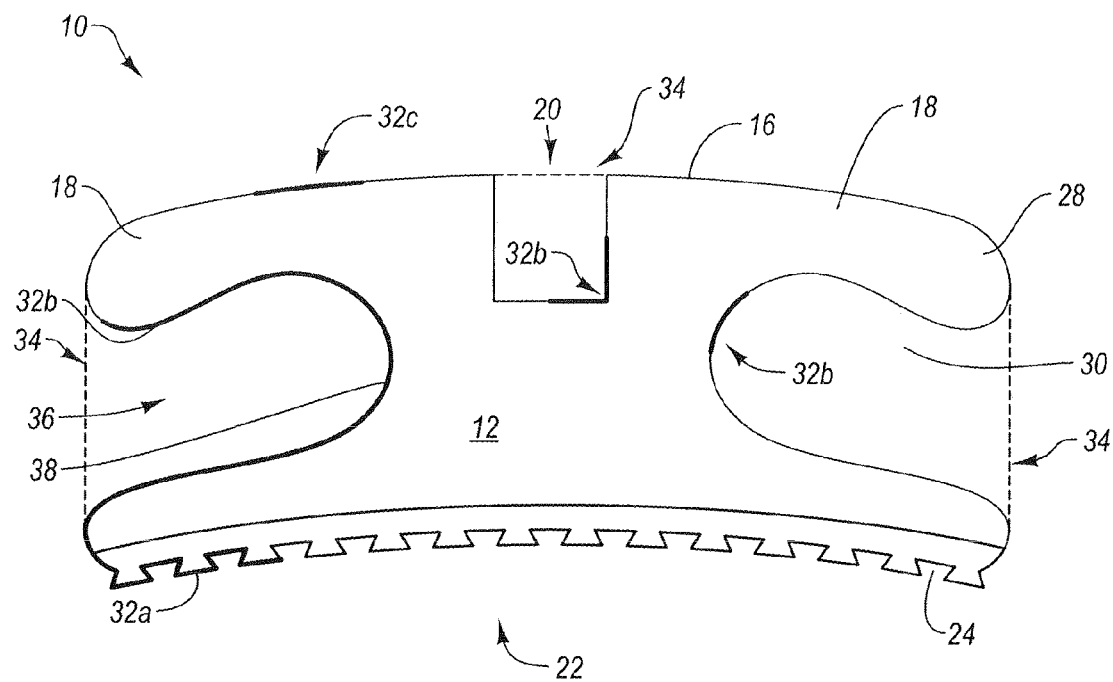
FIG. 1 is a side view illustrating an embodiment of a shaped green body in the form of an orthodontic bracket.

Embodiments of the present invention include initial green bodies comprised of metal or ceramic particles, shaped green bodies prepared from the initial green bodies, sintered bodies prepared from the shaped green bodies, and associated methods of making and using the same. More particularly, embodiments of the present invention include initial green bodies that are shaped with at least one of a stream of energy and/or matter in order to have a desired shape before being sintered into a final hardened article. It should be understood that terminology employed herein is used for the purpose of describing particular embodiments only and is not intended to be limiting.

I. General Definitions

As used herein, the term "green" is meant to refer to the state of an article of manufacture, wherein the article is comprised of a plurality of sinterable particles such as metal or ceramic particles that are held together with an organic binder. As such, an initial green body can be shaped with a stream of energy and/or matter in order to form a shaped green body.

As used herein, the terms "shape," "form," and the like are meant to identify the three-dimensional structure or appearance of an article of manufacture. As such, a green body in the shape of a gear can be construed to indicate that the green body looks like a gear, even though it may have compositions, dimensions, and proportionalities that are different from an actual gear prepared by sintering the gear-shaped green body. For example, a green body shaped like a gear will have the appearance of a gear, but will be about 10% to about 30% larger than the sintered gear. It may also lack sufficient strength to function as intended. Such strength typically develops as a result of sintering.

As used herein, the term "stream-cut" is meant to refer to the process of preparing an object or article to have a desired shape by cutting the object with a stream of energy, such as a laser or electron beam, or a stream of matter such as a water-jet to stream of particles. By being stream-cut, the object or article has been cut so as to alter the shape. A "stream-cut surface" refers to a surface formed by removing sinterable particles by means of at least one of a stream of energy or a stream of matter.

As used herein, the term "laser-cut" is meant to refer to the process of shaping an object or article to have a desired shape by cutting the object with a laser. By being laser-cut, the object or article has been cut with a laser so as to alter the shape.

As used herein, the term "stream of energy" is meant to refer to a beam or flow of energy that is propagated in a substantially linear trajectory. As such, a stream of energy can include a laser beam or other beam of electromagnetic radiation. Additionally, a beam of atomic or subatomic level material such as plasma, ions, or electrons are also considered to be a stream of energy. Examples of atomic or subatomic streams of energy include an electron beam, electrical discharge, plasma beam, ion beam, and the like.

As used herein, the term "stream of matter" is intended to refer to a flow of matter in a substantially linear trajectory, wherein the matter is larger than the atomic level and includes microscopic- and macroscopic-sized particles. Examples of macroscopic streams of matter include water-jet, fluid-jet, chemical-jet, sandblasting, and the like.

Concentrations, amounts, particle sizes and other numerical data may be presented in a range format. It is to be understood that such a range format is used merely for convenience and brevity and should be interpreted flexibly to include not only the numerical values explicitly recited as the limits of the ranges, but also to include all the individual numerical values or sub-ranges encompassed within that range as if each numerical value and sub-range is explicitly recited. For example, sinterable particles can be present in various green body compositions within a range of about 50% to about 98% by total weight. This recited range should be interpreted to include not only the explicitly recited limits of about 50% and about 98%, but also to include such individual compositional percentages, such as 55, 62, 70, and 88, as well as sub-ranges between these individual percentages. This interpretation should apply regardless of the breadth of the range or the characteristic being described, and should apply to ranges having both upper and lower numerical values as well as open-ended ranges recited only one numerical value.

II. Green Body Compositions

In one embodiment, a metal-based composition useful for preparing a green body can include a plurality of sinterable metal particles. The metal particles can include, for example, aluminum, nickel, titanium, copper, cobalt, stainless steel, and the like as well as various alloys thereof. In a more specific example, the metal particles can be comprised of a nickel-titanium alloy powder. More particularly, it is preferable that the metal particles be comprised of a metal that can be pulverized and/or powdered and later sintered. For example, if corrosion-resistant stainless steel gears are desired, a pre-alloyed fine-grained stainless steel powder can be used.

In one embodiment, a ceramic-based composition useful for preparing a green body or intermediate thereof can include a plurality of sinterable ceramic particles. Examples of sinterable ceramic particles, or materials within particles, include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. As such, any sinterable ceramic particle can be used in preparing a sinterable green body in accordance with the present invention.

Accordingly, various types of sinterable metal and/or ceramic powders can be used in preparing an initial green body. In some instances, the use of the articles prepared from sintering the green body will require certain sinterable materials in order to provide the desired or needed physical characteristics. As such, there may be preferences or restrictions on the type of material to be used for a specific type of finished article. In part, this is because different articles may need to withstand forces that are applied during use that impart varying levels of stress or strain. It can be preferable in some cases for the sintered body to have a high level of strength and toughness so as not to be easily damaged during normal use. Alternatively, there may be circumstances that would prefer bendable or high-deflection sintered articles. Some articles may need to withstand very high or very low temperatures. Thus, there are instances where metal particles may be preferred over ceramic particles and vice versa.

Accordingly, the characteristics of the particles used in accordance with the present invention can depend on the structure of the shaped green body as well as the sintered article. In part, the size and surface qualities of the sintered article can determine the size of the particles, e.g., smaller articles or articles having smooth surfaces may require smaller particles. For example, the average diameter of the sinterable particles can generally range from about 0.01 µm to about 5 mm. A preferred smaller particle range is about 0.1 µm to about 50 µm; a more preferred range is about 0.5 µm to about 25 µm; and a most preferred range is about 1 µm to about 10 µm. On the other hand, a preferred larger particle range is about 50 µm to about 5 mm; a more preferred range is about 100 µm to about 1 mm; and a most preferred range is about 0.25 mm to about 0.75 mm. Moreover, it can be beneficial to use a combination of smaller particles within the preferred smaller particle range(s) and within the larger particle range(s).

Additionally, the concentration of sinterable particles within the green body compositions can vary greatly depending on a number of factors, such as particle size, type of metal or ceramic, amount and type of organic binder, and the physical characteristics of the shaped green body and sintered articles prepared therefrom. For example, the sinterable particles may be present in a range of about 25% to about 98% by weight of the green body composition, preferably in a range of about 35% to about 95% by weight, more preferably in a range of about 50% to about 90% by weight, and most preferably in a range of about 60% to about 85% by weight of the green body composition. On the other hand, when metal, ceramics, carbides, or other strengthening fillers are included, the sinterable particles can be present at lower concentrations.

In order to bind the sinterable particles together, the metal or ceramic-based compositions include an organic binder. Examples of organic binders that can be used to bind sinterable particles together in accordance with the present invention include various polymers, polyolefins, silicones, acrylics, latexes, waxes, oils, greases, plasticizers, lignosulfonates, polysaccharides, celluloses and derivatives thereof, starches and derivatives thereof, other natural polymers (e.g., proteins), natural and synthetic rubbers, and the like. More specific examples of polymeric binders can include polypropylenes, polyethylenes, acrylic polymers, polystyrenes, polyethylene-vinyl acetate, polyethylene vinyl alcohol, polyethylene acetate, chlorinated polyethylenes, polyisoprenes, polybutadienes, styrene-butadiene di- and tri-block polymers, polychloroprenes, polyethylene-propylenes, chlorosulfonated polyethylenes, polyurethanes, styrene isoprene polymers, styrene ethylbutylene polymers, styrene butadiene rubber latex, polychloroprene latex, polymethylmethacrylate, polyethylmethacrylate, polydimethylsiloxanes, and the like. It should be recognized that other organic binders known in the art can be used in order to bind the sinterable particles into green body compositions for processing in accordance with the present invention.

Accordingly, the compositions useful in preparing a green body include a binder in an amount and disposition within the plurality of sinterable particles sufficient to hold the sinterable particles together. Additionally, an initial molded green body or intermediate comprised of metal and/or ceramic particles and a binder can be sufficiently pressed or compacted so as to be form-stable and capable of standing freely and being self-supporting. More particularly, the amount and disposition of binder is sufficient for the green body intermediate to be shaped with a stream of matter and/or a stream of energy, such as with a laser, water-jet, or electron beam. Thus, the organic binder can hold the sinterable particles together in the desired shape, and continue to hold the particles together during the shaping process.

Additionally, the concentration of organic binder mixed with the sinterable particles within the green body compositions can vary greatly depending on the aforementioned factors. For example, the organic binder may be present at a concentration range of about 2% to about 75% by weight of the green body composition, preferably in a range of about 5% to about 65% by weight, more preferably in a range of about 10% to about 50% by weight, and most preferably in a range of about 15% to about 40% by weight of the green body composition. As previously described, it should be recognized that any sinterable particle to binder ratio can be used as long as a green body or intermediate is sufficiently held together to be handled and shaped with a stream of energy or stream of matter.

In one embodiment, the organic binder can be intermingled or combined with the sinterable particles in an amount and disposition sufficient to form a flowable particle-binder composition that is capable of being injected into a mold. This flowable particle-binder composition can be premised so as to disperse the binder around and/or between the sinterable particles. This can include adhering the binder onto the particles as well as providing a medium for suspending the particles.

Examples of green bodies and the various processes for manufacturing green bodies in accordance with the present invention as well as the types of articles that can be prepared from shaped green bodies will be discussed in more detail below.

III. Green Bodies

FIG. 1 illustrates an embodiment of a green body 12 in the shape of an orthodontic bracket 10. The green body 12 is comprised of sinterable metal and/or ceramic particles held together with an organic binder, wherein the shape of the orthodontic bracket 10 is defined by an external surface 16. Accordingly, the green body 12 includes at least one tie wing 18 that is characterized as having a lobe 28 that is adjacent to a lobe recess 30. Also, the green body 12 has an archwire slot 20 that is open to the upper (or labial) side. As depicted, the green body 12 includes a bonding surface 22 having a topology that includes a plurality of protrusions and undercuts.

In this embodiment, the exterior surface 16 includes at least one stream-cut (e.g., laser-cut) surface 32a having a topology characterized by a plurality of undercuts 24 formed by removing sinterable particles and binder from the green body 12. In general, features formed from such a feature-forming cut can be either macroscopically visible or microscopically visible. As used herein, the term "macroscopic" can include features that are visual with the naked eye without any magnification. Alternatively, the term "microscopic" as used herein refers to the need for magnification to be used in order to visualize the features.

In one embodiment, the green body 12 can have another stream-cut surface 32b on the external surface 16. This stream-cut surface 32b is cut into the green body 12 so that a significant amount of green material is removed in order to form the shape of the orthodontic bracket 10. Accordingly, the green body 12 can initially have a rectangular cross-sectional area as shown with the dashed-lines 34 (e.g., initial green body). More particularly, a first portion 36 of the green body 12 can be cut away from a second portion 38 of the green body, which thereby forms the laser-cut surface 32b at the cut.

Additionally, a minor stream-cut surface 32c can be made to remove only a minimal amount of green body material or to refine a previous cut. Thus, a feature-forming stream-cut surface 32a, significant stream-cut surface 32b, and/or a minor stream-cut surface 32c can be part of the external surface 16 of a green body shaped by being stream-cut according to the invention.

Figure 2:
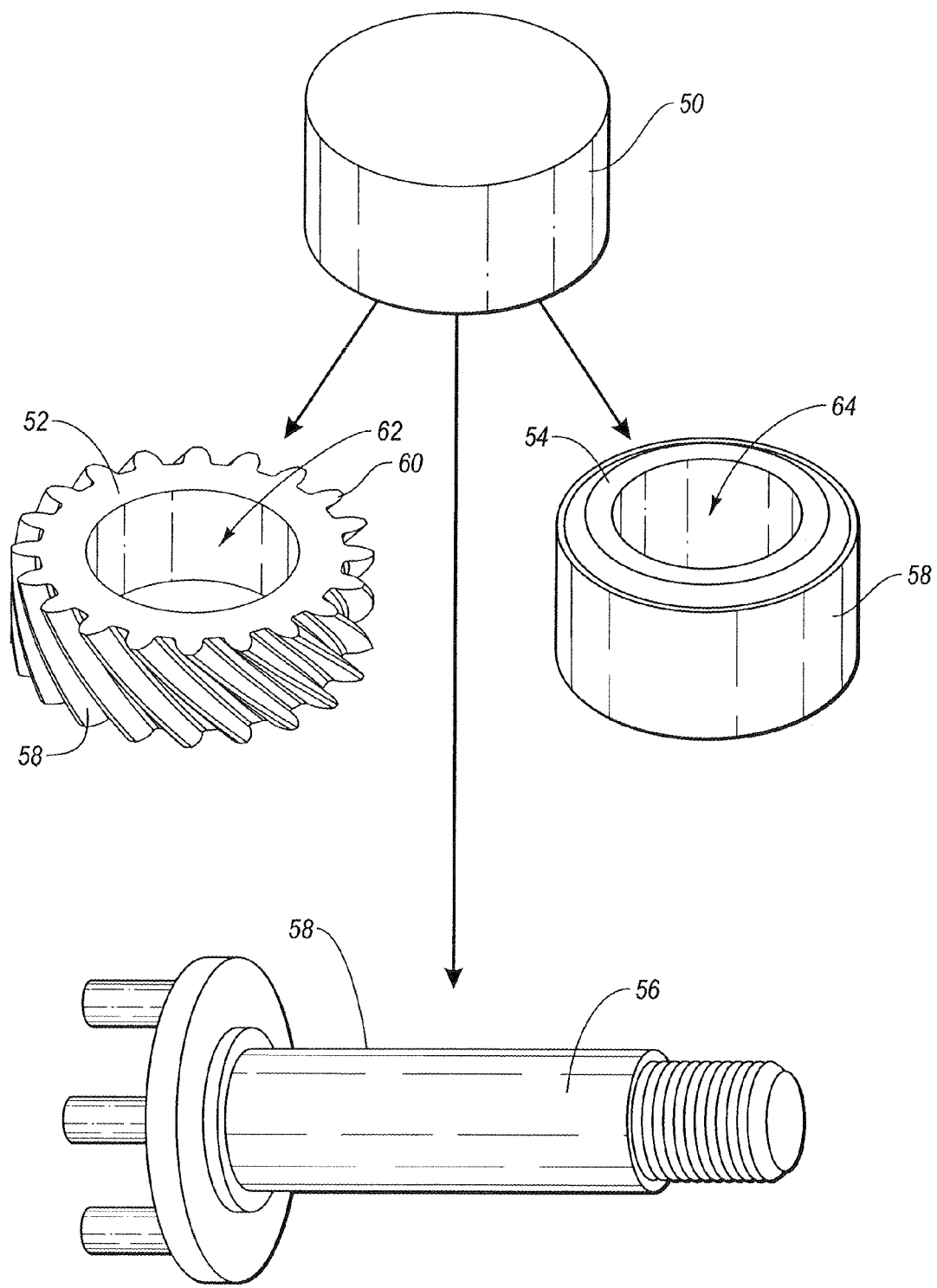
FIG. 2 is a schematic diagram that illustrates different embodiments of shaped green bodies that can be shaped from a single initial green body by stream-removal of sinterable particles therefrom.

FIG. 2 illustrates additional embodiments of articles that can be formed from a green body 50. A single initial green body 50 can be stream-cut into a shaped green body having the shape of a gear 52, roller 54, spindle 56, or any other desired article. This can be done by stream-cutting process that essentially forms the desired shape from the initial green body 50 by cutting away the excess material. Thus, a substantially cylindrical-shaped initial green body 50 can be cut into a myriad of green body shapes.

Accordingly, the initial green body 50 can be shaped by a stream-cutting process so as to form a stream-cut surface 58. As such, the stream-cut surface 58 can include the entire external surface so that the shape of the gear 52, which includes gear teeth 60 and an aperture 62, can be formed by cutting the green material with a stream of energy or stream of matter. Thus, the teeth 60 and aperture 62 can each be defined by a stream-cut surface 58.

Similarly, the stream-cut surface 58 can be cut into the initial green body 50 so as to form the shape of a roller 54. As shown, the roller 54 includes an annular outer stream-cut surface 58 that is substantially smooth. Also, an aperture 64 defined by a smooth stream-cut surface 58 can be bored through the initial green body 50.

Alternatively, a spindle 56 having a stream-cut surface 58 can be stream-cut from the initial green body 50.

While various embodiments of shaped green bodies have been depicted and described, the present invention is not limited to such shapes. Accordingly, a shaped green body can be any shape that can be cut and sintered as described herein. That is, any shape or article prepared from sintering can be prepared as a shaped green body in accordance with the present invention.

Figure 3A:
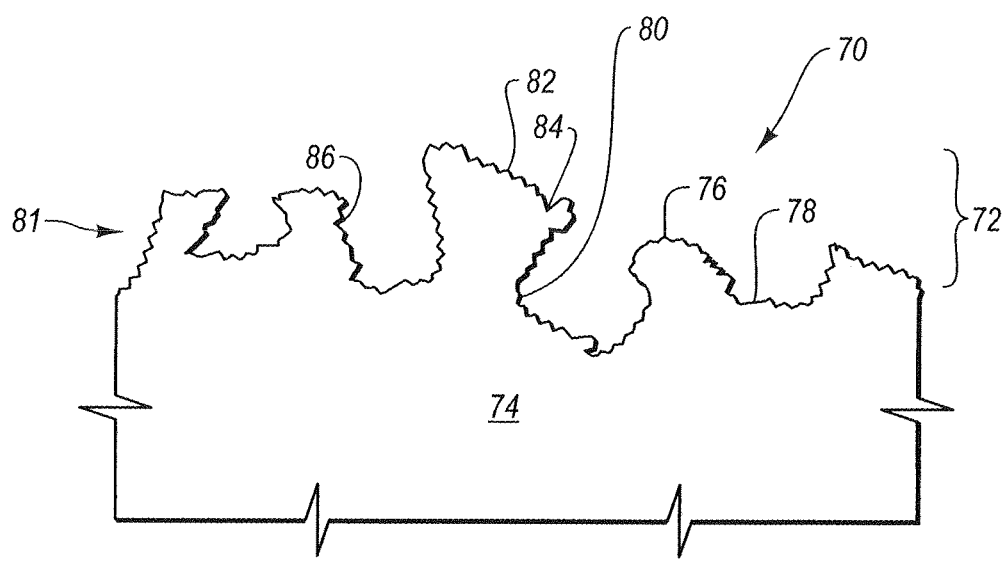
FIGS. 3A and 3B are cross-sectional view of the embodiments of exemplary morphologies of a stream-cut surface.
Figure 3B:
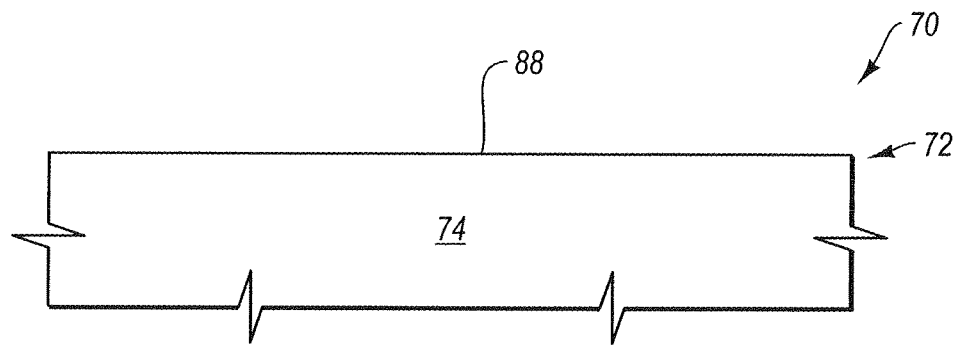

FIGS. 3A and 3B illustrate embodiments of a stream-cut surface 70. The stream-cut surface 70 of FIG. 3A includes a topology 72 that defines features on the exterior surface of a green body 74. In this embodiment, the topology 72 includes a plurality of macroscopic irregular elevations, which can be in the form of protrusions 76, recesses 78, and/or undercuts 80, and result in a substantially uneven or rough surface 81. The larger irregular elevations can also include microscopic or smaller irregular elevations, which can be micro-protrusions 82, micro-recesses 84, and micro-undercuts 86.

Alternatively, as shown in FIG. 3B, the stream-cut surface 70 can be cut with a stream of energy or stream of matter in a manner than results in a topology 72 that defines a substantially smooth surface 88. Thus, the green body 74 can be configured to have a topology or surface ranging from substantially uneven (FIG. 3A) through substantially smooth (FIG. 3B).

The topology 72 characterized by the uneven or rough surface 81 or smooth surface 88 can be comprised of a binder holding a plurality of sinterable particles together to form the green body 74. In one embodiment, a portion of metal particles on the topology 72 are melted together to form a melted surface layer. In another embodiment, the sinterable particles on the topology 72 are adhered together with melted binder.

In yet another embodiment, a portion of the topology 72 includes a charred or blackened layer, especially when formed by a stream of energy such as a laser. The charred or blackened layer can be characterized by surface features that result from the vaporizing, melting, and/or burning of the binder that accompany the process of cutting the green body 74 with the stream of energy that heats the surface to a hot temperature.

IV. Manufacturing Green Bodies and Sintered Articles

FIGS. 4-10 illustrate various schematic diagrams of embodiments of processing systems and equipment that can be used during the formation of green bodies and sintered articles prepared therefrom. It should be recognized that these are only examples of schematic representations of processing systems and equipment, and various modifications can be made thereto in order to prepare the inventive green bodies and sintered articles. Accordingly, the various systems and equipment currently known or later developed for preparing most types of sinterable green bodies and sintered articles are considered to be included within the scope of this disclosure. Also, the schematic representations should not be construed in any limiting manner to the arrangement, shape, size, orientation, or presence of any of the features described in connection therewith. With that said, a more detailed description of examples of some of the systems and equipment that can prepare the green bodies and sintered articles in accordance with the present invention is now provided.

Figure 4:
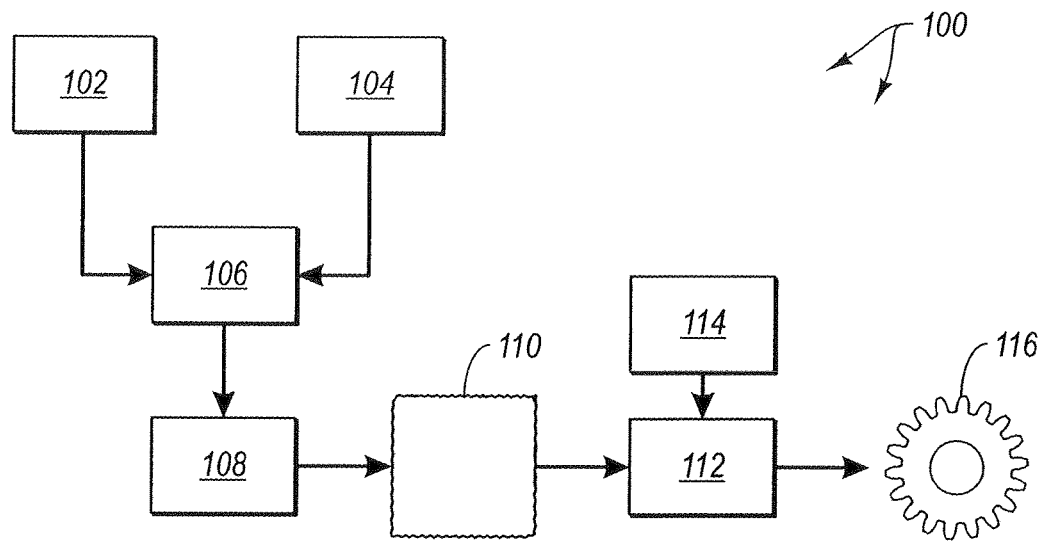
FIG. 4 is a schematic diagram that illustrates an embodiment of a system for preparing a shaped green body.

FIG. 4 is a schematic diagram illustrating a general embodiment of a shaping system 100 for preparing a shaped green body from an initial green body. Initially, the sinterable particles are obtained from a particle supply 102, and the organic binder is obtained from an organic binder supply 104. The sinterable particles and organic binder are then introduced into a mixing apparatus 106 to prepare a mixture. The mixture is then introduced into a molding apparatus 108, which forms an initial green body or intermediate 110 of a desired initial shape. The initial green body 110 can be characterized as having an exterior surface that is substantially in the shape of the mold cavity defined by the molding apparatus 108.

The initial green body or intermediate 110 having the shape of the mold cavity is then supplied into a stream-cutting apparatus 112. The stream-cutting apparatus 112 may at some point be in communication with a three-dimensional ("3-D") virtual image generator 114, which can create a 3-D virtual image of the desired shape of the shaped green body 116. Alternatively, the 3-D virtual image can be created within the 3-D virtual image generator 114 and then stored on a data storage device, which is then provided to the stream-cutting apparatus 112.

In any event, the stream-cutting apparatus 112 is able to stream-cut the initial green body 110 into a shaped green body 116. Preferably, the stream-cutting apparatus 112 uses computer-guided technology to direct a stream of energy and/or a stream of matter so that a precise shape is formed into the green body material. As depicted, the shaped green body 116 can be prepared into the shape of a gear, or any other desired stream-cut shape.

Figure 5:
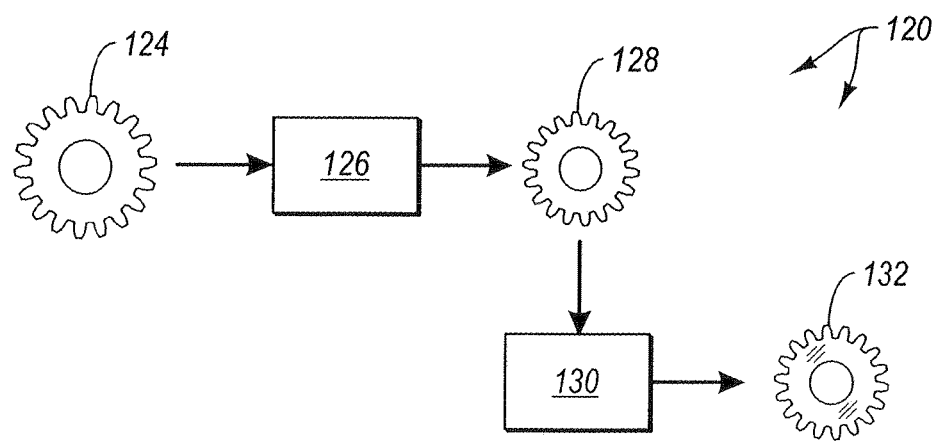
FIG. 5 is a schematic diagram that illustrates an embodiment of a system for preparing a sintered body from a shaped green body.

FIG. 5 is a schematic diagram that illustrates a general embodiment of a sintering system 120 for sintering a shaped green body into a sintered body. A shaped green body 124 may be obtained by employing a shaping system 100, as depicted in FIG. 4. Alternatively, various other embodiments of shaping systems in accordance with the present invention can provide the shaped green body 124. In any event, the shaped green body 124 is introduced into a sintering apparatus 126. The sintering apparatus 126 then sinters the sinterable particles together and removes the binder from the interstitial spaces. In some instances it can be preferable for the binder to be removed by being melted away or vaporized such as through a de-binding process.

After sintering the green body material, a sintered body 128 is removed from the sintering apparatus 126. A comparison of the sintered body 128 with the shaped green body 124 shows that sintering has reduced the volume of the article by about 10% to about 30% according to a preferred embodiment. Optionally, the sintered body 128 may then be processed through a finishing apparatus 130 that can further refine the sintered body into a finished article 132. Many processes can be used to finish a sintered article, which depend on the nature of the finish. Examples of such finishing processes include grinding, sanding, shot peening, powder coating, painting, and the like.

V. Manufacturing Particle-Binder Compositions

Figure 6:
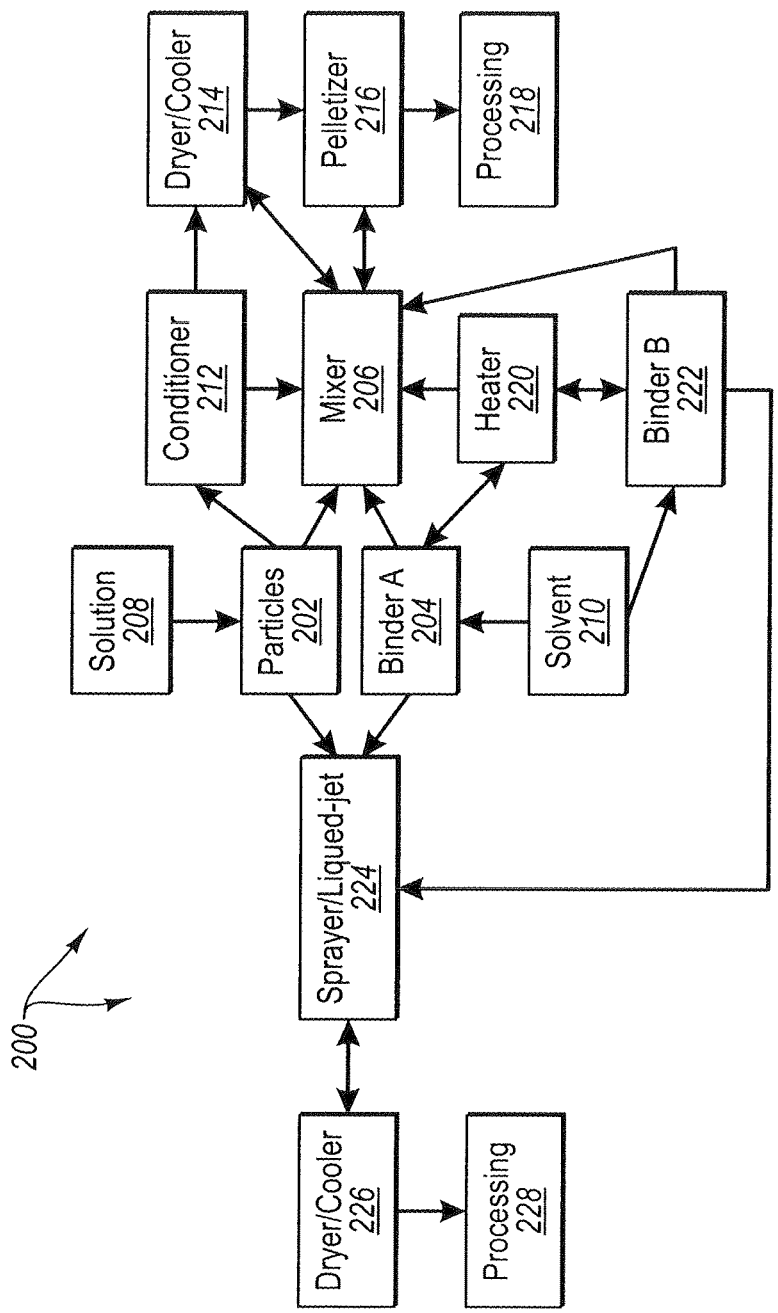
FIG. 6 is a schematic diagram that illustrates an embodiment of a system for processing a particle and binder composition used to form initial green bodies.

FIG. 6 is a schematic diagram illustrating embodiments of a particle-binder processing system 200 in accordance with the present invention. The various embodiments of particle-binder processing system 200 described below can be represented by the general mixing apparatus 106 described in FIG. 4. More particularly, the particle-binder processing system 200 can be used to mix the particles and binder together in order to form a mixture that is capable of being introduced into a mold for preparing a green body in accordance with the present invention.

In one embodiment, sinterable particles can be kept in a particle storage container 202 such as a container, storage bin, hopper, mixer, and the like. A suspension solution for suspending the sinterable particles can be kept in a suspension container 208. Additionally, binder A can be similarly kept within a binder storage container 204, and a binder solvent for dissolving or suspending the binder can be kept in a solvent container 210.

Accordingly, particles from container 202 can be combined with the suspension solution from container 208. The suspension solution is compatible with the particles so as to form a particle suspension or other fluid composition that is capable of being processed for preparing the particle-binder composition. The suspension solution can be comprised of an organic solvent or water, and can include cellulose ethers to impart Non-Newtonian shear characteristics or thickening to hold the particles in suspension. As such, the particles and suspension solution can be combined in the particle container 202, suspension container 208, or a mixer 206.

Similarly, binder A from container 204 can be combined with the solvent from container 210, wherein the combining can be performed within the binder A container 204, solvent container 210, or the mixer 206. As such, the solvent can be mixed with binder A to either dissolve the binder A or form a flowable suspension therewith. The binder A and solvent mixture can be useful in preparing the particle-binder composition with the particles and with or without the suspension solution.

In one embodiment, the suspended particles are supplied into mixer 206. Additionally, binder A suspended or dissolved in the solvent can also be supplied into mixer 206. Mixer 206 can be a high sheer mixer or a low speed mixer that is configured to form a composition comprised of particles and binder A. Additionally, the suspension solution and/or solvent can enhance mixing by being either miscible or immiscible. In either case, a particle-binder composition can be prepared in the mixer 206. Alternatively, the particles without the suspension solution are mixed in the mixer 206 with binder A with or without the solvent.

In one embodiment, the suspended particles can be combined with the binder A in mixer 206 without the binder solvent. As such, binder A can be heated by heating unit 220 in a manner that liquefies binder A. By liquefying binder A with the heating unit 220, the binder can be easily manipulated and injected into mixer 206. As such, the heating unit 220 can be configured to supply heat to the binder A container 204, or alternatively, binder A can be supplied into the heating unit 220. In any event, binder A is heated so as to be flowable, wherein a fluid binder can be easily injected into mixer 206. In the instance binder A is liquefied by heat without the aid of solvent, the particle suspension can enable increased mixing between the particles and binder A. Alternatively, the particles without the suspension solution are mixed with the heated binder in the mixer 206.

In one embodiment, dry particles from container 202 and binder A from container 204 can be supplied directly into mixer 206 without any suspension solution, solvent, or heat. In this case, mixer 206 can be a dry granulizing mixer, which can granulize and combine the particles and binder A into a homogenous granulized composition. Accordingly, such a granulized composition can be further processed in accordance with the present invention.

In one embodiment, particles from container 202 with or without the suspension solution from container 208 can be supplied into a conditioning vessel 212. The conditioning vessel 212 can contain a conditioner (e.g., conditioning composition) for conditioning the particles in a manner to enhance the mixing with the binder. Such a conditioner can be any of various waxes, polyolefins, dispersants, rheology-modifying agents, surfactants, and like materials so as to enhance the ability of the particles to be combined, coated, and/or interspersed within binder A. In one embodiment, the conditioner can be an organic binder. After mixing, the conditioner can at least partially coat the particles in a manner that increases the interaction between the particles and binder A. Thus, particles that have been conditioned in the conditioner 212 can then be supplied into mixer 206 along with binder A.

On the other hand, after the particles are supplied into the conditioning vessel 212, it may be beneficial to introduce the conditioned particles into a dryer/cooler unit 214. As such, the conditioner may comprise a volatile solvent so that when the dryer 212 is heated, the solvent is vaporized leaving dry conditioned particles. On the other hand, the conditioning vessel 212 may be heated so that the cooler 214 cools the conditioned particles before being further processed. Either the dried or cooled conditioned particles can be further processed by being mixed in mixer 206.

In any event, independent of how the particles or binder A have been processed, mixer 206 can be configured to provide a substantially homogeneous composition comprised of the particles and binder A.

In one embodiment, mixer 206 can be configured to be an extruder. Accordingly, such an extruder can be a single screw extruder, twin screw extruder, or a piston-type extruder. This can be beneficial in order to produce an extrudate comprised of particles and binder A. The extruder can include heating elements to increase the temperature of the particle-binder composition when thermoplastic binders are used. The heating elements can vaporize any solvents, and also increase the composition to a temperature sufficient for being extruded.

In one embodiment, independent of how the particle-binder composition is prepared, such a composition can be supplied into the dryer/cooler 214. The dryer 214 is configured to remove any solvent or other volatile substances from the mixture. Accordingly, the dried composition can have a moisture content less than about 20% by wet weight, more preferably less than about 10% by wet weight, and most preferably less than about 5% by wet weight. Alternatively, the cooler 214 can decrease the temperature of a heated mixture (e.g., extrudate) such that it can be further processed. The cooler 214 can decrease the temperature to about 35° C., or more preferably about 30° C., and most preferably less than about 25° C.

In one embodiment, the composition obtained in mixer 206 may forego any drying/cooling, and can be directly supplied into pelletizer 216; especially when in the form of an extrudate. Alternatively, the dried or cooled composition obtained from the dryer/cooler 214 can be supplied into pelletizer 216. In any event, the particle-binder composition can be pelletized so as to form small pellets having various sizes or shaped. Such shapes can be relatively spherical, uneven, and/or jagged.

Pelletizer 216 can be configured for cutting the dried or cooled particle-binder composition into pellets or beads having a variety of sizes. For example, pelletizer 216 can form pellets having an average diameter from about 0.2 mm to about 2 cm, more preferably in range from about 0.3 mm to about 1 cm, and most preferably in a range from about 0.5 mm to about 0.8 cm. However, any pellet size can be obtained because the size of the shaped green body and its surface characteristics can be determinate of the pellet size.

In another embodiment, it could be preferable for the particle-binder composition to be removed from the mixer 206 in a form or a consistency useful for further processing 218 into a green body intermediate in accordance with the present invention.

In one embodiment, additional binder B can be kept in a binder B storage container 222, and can be utilized in order to form a particle-binder system having at least two-types of binders. As such, it can be beneficial to form a particle-binder A composition as described herein, and then further process such a composition with additional binder B. Binder B obtained from container 222 can be processed similar to binder A from container 204 by being dissolved or suspended in a solvent from container 210, or by being liquefied by heating unit 220. Accordingly, binder B can be supplied into mixer 206 with the particle-binder A composition, which can form a dual-binder composition.

Alternatively, after particle-binder A pellets have been prepared in pelletizer 216, such pellets can be supplied into mixer 206 along with binder B. The pellets obtained from pelletizer 216 can be substantially coated with binder B, or become suspended within binder B. Also, the particles combined with binder A and binder B can then undergo further processing as described herein after being mixed in mixer 206.

In another embodiment, processing the particles and binders so as to form a particle-binder composition can be performed in a sprayer/liquid-jet apparatus 224. As such, the particles from container 202 can be supplied into the sprayer/liquid-jet apparatus 224. Optionally, such particles can be supplied by a conveyer or other means of holding the particles so that they can be sprayed with a liquefied binder. This can include a vibrating conveyor or other type of holder such that the particles can be sprayed easily on all sides or surfaces.

In one embodiment, the sprayer/liquid-jet apparatus 224 can have a column-like spray tower configured with nozzles to spray the binder. In this embodiment, the particles can be supplied into the sprayer/liquid jet apparatus 224 by being dropped from the top of the spray tower so as freefall past the nozzles spraying the binder so as to at least partially coat the particles. Additionally, any of the spray processes can be performed with particles that have been suspended or conditions, or previously coated with a binder.

Independent of the particle-binder composition formed within the sprayer/liquid-jet apparatus 224, such a composition can be supplied into a dryer/cooler apparatus 226 so as to dry and remove any access volatile solvent, or to cool the particle-binder composition. As such, the particle-binder composition can be dried or cooled with apparatus 226 so as to be prepared for further processing 228 in accordance with the present invention.

While embodiments of equipment, systems, and methods for preparing a particle-binder composition have been described in connection with FIG. 6, various other equipment, systems, and methods can be used so as to form a particle-binder composition in order to prepare an initial green body or intermediate. As such, the processes of preparing an initial green body will be discussed in further detail below.

VI. Molding Green Bodies

Referring now back to FIG. 4 and more particularly to the molding apparatus 108, embodiments of systems and processes for molding green bodies are described in greater detail. As such, the molding apparatus 108 can receive any of the particle-binder compositions prepared in accordance with the present invention and/or described in connection with FIG. 6.

In any event, the particle-binder composition can be supplied into the molding apparatus 108, which can be operated by any of the well-known schemes for providing a molded article. As such, the molding apparatus 108 can be operated at high temperatures and/or at high pressures so as to form a molded body. It can be beneficial to operate the molding apparatus in a manner that generates a high pressure so that the particles can be tightly pressed together. In this manner, any voids, air pockets, or other anomalies within the binder the particle composition can be pressed out and removed so that a dense form-stable molded article can be prepared.

In one embodiment, the molding apparatus 108 can be configured to have movable mold bodies that can compress the particle-binder composition during molding. In this manner, a first volume of the particle-binder composition can be supplied into the molding apparatus 108 until it is substantially full, and then by a compression molding technique, the molding apparatus can decrease the volume of the particle-binder composition. By compressing the composition, a more dense molded green body intermediate can be obtained. Such compression can also be achieved by increasing the pressure within the mold by either using some type of extruder apparatus such as a piston extruder or by decreasing the volume of the mold cavity within the molding apparatus 108.

In one embodiment, a method of molding a green body intermediate can include injecting a particle-binder composition into a mold under high pressure and/or temperature such as in injection molding. Alternatively, the binder and sinterable particles can be injected into a mold as separate feed streams that are delivered at different times or simultaneously. When the particles and binder are injected as separate feeds, it may be advantageous for the binder to easily coat the particles by having a high work of adhesion with respect to the particles, or to be heated and mixed with the particles in the mold.

Additionally, the molding apparatus 108 can be configured to operate by injection molding, casting molding, compression molding, thermal molding, or any other molding technique.

In one embodiment, the green body intermediate can be formed by increasing the temperature and/or pressure so that the sinterable particles and binder are pressed together into the shape of the mold cavity. Accordingly, the mold can increase the temperature of the particles and binder from about 80° C. to about 400° C., and more preferably from about 100° C. to about 380° C., and most preferably about 120° C. to about 340° C. Also, the particles and binder can be pressed together at a pressure range of about 2 MPa to about 200 MPa, more preferably about 10 MPA to about 200 MPa, and most preferably about 100 MPa to about 200 MPa.

The shape of the mold cavity within the molding apparatus 108 can be a general shape such as a cube, cylinder, sphere and the like. Alternatively, the mold cavity can have a complex shape that is similar to the shape of the final article prepared from the molded green body intermediate.

Moreover, many variations can be made in the molding process performed within the molding apparatus 108 so as to obtain a molded article that is a green body intermediate.

VII. Generating Virtual Images

Figure 7:
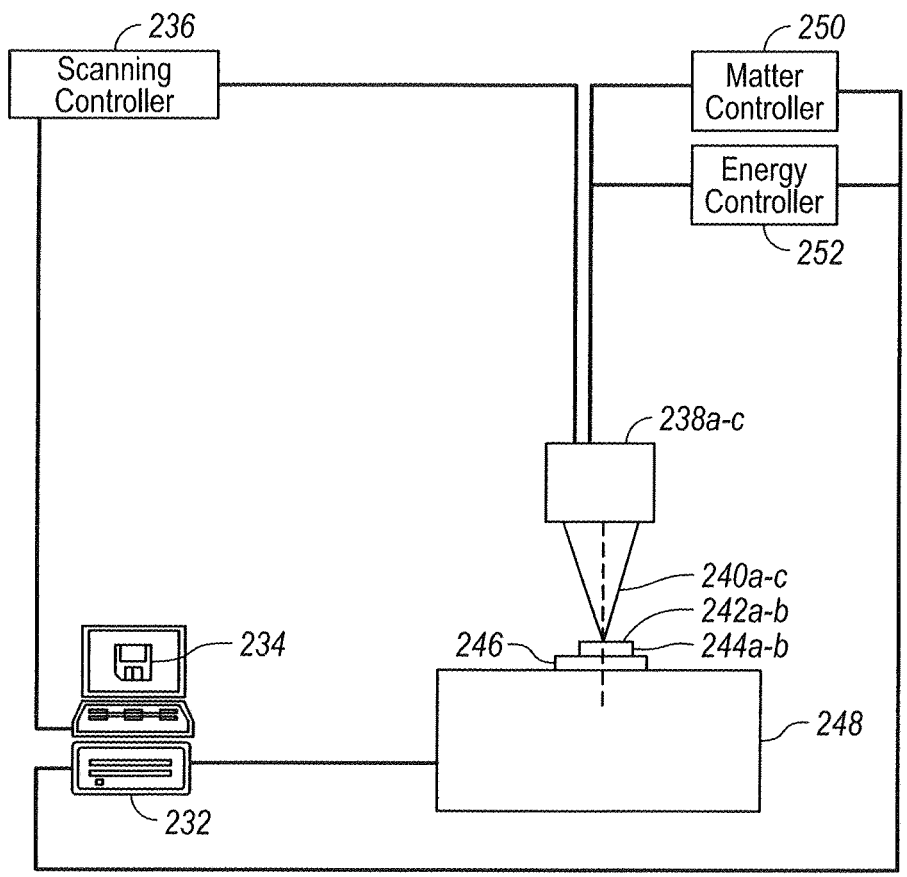
FIG. 7 is a schematic diagram that illustrates an embodiment of a scanning and/or shaping system.

FIG. 7 is a schematic diagram that illustrates a scanning system 230 (e.g., scanning and shaping system 230) in accordance with the present invention. Such a scanning system 230 can be used as at least part of the three-dimensional ("3-D") virtual image generator 114 of FIG. 4. Accordingly, the scanning system 230 includes a computer system 232 in order to control the movement of the various scanning components by providing control data to the scanning controller 236. Also, the computer system 232 can control any data acquisition, and direct any image data generated during scanning to be saved on a data storage device 243. Data storage devices 234 is well known in the art, and can include, but is not limited to, floppy drives, hard disk drives, magnetic disk drives, optical disc drives, read access memory ("RAM"), read-only memory ("ROM"), and the like. The scanning system can operate similarly to any of the various well-known and later developed scanning protocols.

In any event, the scanning controller 236 is in communication with the computer system 232. This allows the computer system 232 to be programmed by a user in order to manipulate and control the performance of the scanning controller 236. After a scanning protocol is input into the scanning controller 236, the scanning controller 236 controls an emitter 238, which is configured to emit a scanning beam 240a towards the surface 242 of the body being scanned 244. A scanning beam 240a directed towards the surface 242 of the body 244a can enable the acquisition of 3-D image data. Such data acquired by the scanning controller 236 can be stored on the memory storage device 234 as raw data or data that has been manipulated to generate a virtual 3-D image of the body 244a.

Additionally, in order to facilitate the scanning of the body 244a the scanning system 230 can include a turret 246 that can rotate the body 244a as well as a mechanical feature 248 that can enable lateral movement in the x, y, and z axes as well as rotate around the x, y, and z axes. As such, a 3-D virtual image can be obtained and stored within the memory storage device 234 so as to be usable in various computer-assisted drawing programs ("CAD"). By acquiring a 3-D virtual image of the body 244a, a user can manipulate such a virtual image in order to obtain an exact or precise 3-D virtual image of the desired shape of the green body and sintered article.

In any event, a mockup of the desired finished article can be placed within the scanning system 230 so that destructive or non-destructive scanning can be used to create a virtual image. Such destructive and non-destructive scanning technologies as well as the associated equipment and software that are used to generate three-dimensional virtual images are well known. Additionally, it can also be possible to create a 3-D image using a CAD program so that the shape of the green body is created entirely from a virtual image without a mockup. Also, CAD programs can be used to take any virtual image and alter the shape and size in order to provide the desired shape of the green body.

VIII. Stream-Cutting Green Bodies

Referring again to FIG. 4, more particular details for the embodiments of the stream-cutting apparatus 112 are described in accordance with the present invention. The stream-cutting apparatus 112 can be configured to have or use a variety of stream-cutting techniques. Such stream-cutting techniques can utilize streams of energy and/or streams of matter. The streams of energy include photons, electromagnetic radiation, atomic, and sub-atomic materials, as described above. On the other hand, the streams of matter are considered to include materials larger than atomic scale particles, and can be microscopic or macroscopic in size. In any event, the stream-cutting apparatus 112 is designed to direct a stream of energy or a stream of matter at the initial green body 110 prepared in the molding apparatus 108, as described above in connection with FIG. 4.

Referring again to FIG. 7, the schematic diagram also depicts an embodiment of a shaping system 230 (e.g., scanning and shaping system). The shaping system 230 can be employed within the stream-cutting apparatus 112 of FIG. 4. The shaping system 230 can optionally be combined with the scanning system 230 so as to be a scanning and shaping system 230, as described in more detail below. In any event, the shaping system 230 can acquire the 3-D virtual image previously generated from the computer system 232 or the data storage device 234.

The shaping system 230 can include a matter controller 250 and/or an energy controller 252 in communication with the computer system 232. The matter controller 250 can enable the emitter 238b to emit a stream of matter 240b to be directed at a surface 242b of a green body 244b that is being shaped. The matter controller 250 can control the emitter 238 so that a stream of matter 240b, such as chemicals, water, and other particulates, can be directed at the green body 244b. The stream of matter 240b can shape the green body 244b in accordance with the virtual image stored in the data storage device 234 of the computer system 232.

In another embodiment, the energy controller 252 can control the emitter 238c to emit a stream of energy 240c, such as a laser, electron beam, ion beam, or the like, towards the green body 244b to obtain a shape in accordance with the virtual image.

In view of the foregoing general description of a shaping system in accordance with the present invention, the various types of streams of energy and streams of matter that can be used therein will now be described in more detail. As such, the following embodiments of stream-cutting apparatuses can be employed within the stream-cutting apparatus 112 of FIG. 4 as well as in the shaping system 230 of FIG. 7.

In one embodiment, the stream of energy can cut and shape the green body intermediate by generating heat at the site where the stream intersects the green body material. As such, energy can be used to generate heat in order to have a thermal interaction with the binder and the sinterable particles. The thermal interaction can elevate the local temperature to a point which can cut, de-bind, melt, and/or vaporize portions of the binder-particle composition from the rest of the bulk green body material.

Accordingly, one embodiment of the stream-cutting apparatus can operate and shape the green body intermediate by thermal interactions. As such, any of the thermal processes described herein can be used for thermal-cutting. For example, such thermal interactions can arise from laser beam treatment, laser beam machining, electron beam machining, electrical discharge machining, ion beam machining, and plasma beam machining. Thus, a stream-cut surface can be a laser-cut surface, electron beam-cut surface, electron discharge-cut surface, ion beam-cut surface, or a plasma beam-cut surface.

In one embodiment, since the green body compositional concentrations are known to be comprised of a substantial amount of binding material, the thermal cutting process can require less energy in comparison to similar techniques used for sintered or otherwise hardened metal or ceramic articles. As such, by knowing the thermal properties of the binder, precise energy requirements can be calculated so that the thermal beam provides the appropriate or minimum energy for melting and/or vaporizing the binder without significantly melting or point-sintering the sinterable particles. Alternatively, the energy can be increased so as to melt and/or point sinter the sinterable particles.

For example, laser beams are a common form of a stream of energy that can be used in the stream-cutting apparatus 112. Typical laser-cutting machines can accurately produce complex exterior contours in the green body because a laser beam is usually between about 0.02 mm to about 0.2 mm in diameter at the cutting surface and can have a power that ranges up to about 2,000 watts; however, benefits of the current invention include the use of lower powered lasers. Additionally, there are instances where a laser is preferred over all other stream-cutting techniques because of the nature of the resulting article as well as the characteristics of the green body.

Accordingly, a laser can cut the green bodies, wherein the power of the laser or the heat generated can depend upon the composition of the material to be cut. The ability to vary the laser power arises due to the use of different binders and/or sinterable particles. The laser power is defined as the rate of which energy is delivered by the beam and is usually measured in units as joules/second or watts.

For example, lasers typically used in laser surgery have a power on the order of about 10 watts, and such a low wattage can be used to melt some binders to shape the green body. On the other hand, lasers typically used in cutting hardened steel, such as YAG or eximer lasers, can have a power of about 2,000 watts. Accordingly, green bodies with softer binders can be shaped with lasers operating below about 500 watts, more preferably below about 400 watts, and most preferably below about 200 watts. Alternatively, harder binders or additionally melting and/or vaporizing the metal or ceramic particles can use lasers operating above about 500 watts, more preferably above about 750 watts, and most preferably above about 1,000 watts.

In one embodiment, electrical discharge machining is used to shape a green metal body. As such, electrical discharge machining is capable of cutting all types of conductive materials such as exotic metal including such as titanium, hastaloy, kovar, inconel, hard tool steels, carbides, and the like. In electrical discharge, the main interaction between the stream of energy and the green body is thermal, where heat is generated by producing electrical discharges. This can lead to the green body material being removed by melting and evaporation. Some examples of electrical discharge machining include wire electron discharge machining, CNC-controlled electrical discharge machining, sinker electrical discharge machining, small hole discharge machining, and the like.

In another embodiment, the stream-cutting apparatus 112 can use a charged particle beam, wherein charged particle beams are exemplified by electron beams and ion beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams can be useful for cutting and shaping of the green bodies, as described herein. Additionally, there are some instances where electron beams or ion beams are preferred over other cutting techniques.

In one embodiment, the stream-cutting apparatus 112 can use a stream of chemical matter in order to shape the green body. Chemical-jet milling, for example, provides selective and controlled material removal by jet and chemical action. As such, the process is similar to water-jet cutting, which is described in more detail below. In any event, chemical-jet milling can be useful for removing various types of binders from the bulk green body material, which provides intricate shaping capabilities. More particularly, binders that can be chemically dissolved by certain solutions or solvents can be chemically milled by directing a stream of the reactive chemicals.

In another embodiment, electrochemical shaping can be based on a controlled electrochemical dissolution process similar to chemical-jet milling a green body comprised of a metal sinterable particle. As such, the green metal body is attached to an electrical source in order to allow an electrical current to assist in the shaping.

In one embodiment, it can be beneficial for the stream-cutting apparatus 112 to be configured as a hydro-cutting apparatus or water-jet cutter. Hydro-cutting is essentially a water-jet technology that uses the high force and high pressure of a stream of water directed at the green body in order to cut and shape the green body as desired. Hydro-cutting can be preferred over some of the other stream-cutting technologies because it can be free of heat, flame, and chemical reactions, and can provide a precise cold shaping technique. However, heated water with or without being doped with reactive chemicals can also be used.

A typical hydro-cutting apparatus for hardened materials can use about 2.5 gallons of water per minute directed at the green body at about 40,000 psi as a single stream. For example, a hydro-cutting apparatus in accordance with the present invention can use from about 0.25 gallon/minute to about 15 gallons/minute, more preferably from about 0.5 gallon/minute to about 10 gallons/minute, even more preferably from about 1 gallon/minute to about 5 gallons/minute, and most preferably about 2 gallons/minute to about 4 gallons/minute. However, it should be recognized that higher or lower flow rates can be used, and depend on the diameter and pressure of the flow.

Additionally, the hydro-cutting apparatus can jet the water at a force that ranges from about 50 psi to about 60,000 psi. This is because there are instances where lower pressures, such as from about 50 psi to 500 psi, can be used to ablate softer binders, and some instances where more durable and harder binders may use from about 15,000 psi to about 60,000 psi, especially when shaping larger parts such as automobile or airplane parts or construction materials. Additionally, water-jets similar to those used for washing purposes can jet the water at about 1,000 psi to about 5,000 psi in order to shape a green body bound with a binder of medium hardness. Thus, a wide range of water pressures can be employed.

Moreover, the stream of water can be used at greatly varying diameters. This is because the diameter of the flow drastically affects the intricacy of the cutting or etching, where etching green bodies for microelectronic circuit boards can require an extremely fine diameter flow as small as about 0.5 mm, and carving a rough shape and/or a larger article such as a tractor wheel rim can use a flow diameter of about 2.54 cm. However, there are instances where the use of a larger diameter, such as about 6 mm, is first employed for rough shaping before fine and intricate shapes are made with a jet of about 1 mm. Also, it is contemplated that larger or smaller diameter water-jets can be used.

Additionally, hydro-cutting can be enhanced by the introduction of particulate materials into the water feed line. As such, some hydro-cutting techniques utilize garnet or other rigid and strong materials in order to apply an abrasive cutting force along with the force applied by the water itself. Also, the hydro-cutting process in the present invention can be used with or without inclusion of such abrasives.

Additionally, one of the benefits of hydro-cutting is the ability to reutilize and recycle the spent water-jet material. As such, the green body materials can be easily separated from the spent water, thereby enabling the recycling and reuse of the water during the hydro-cutting process.

In one embodiment, sandblasting, which fits into the regime of the stream of matter cutting, can be used to shape green bodies by projecting a high energy stream of sand particles at the green body material. Sandblasting cuts materials similar to hydro-cutting, especially when the water-jet is doped with abrasive particulates. Additionally, various other particulate streams other than sand can be used in the stream-cutting techniques and machinery.

Figure 8:
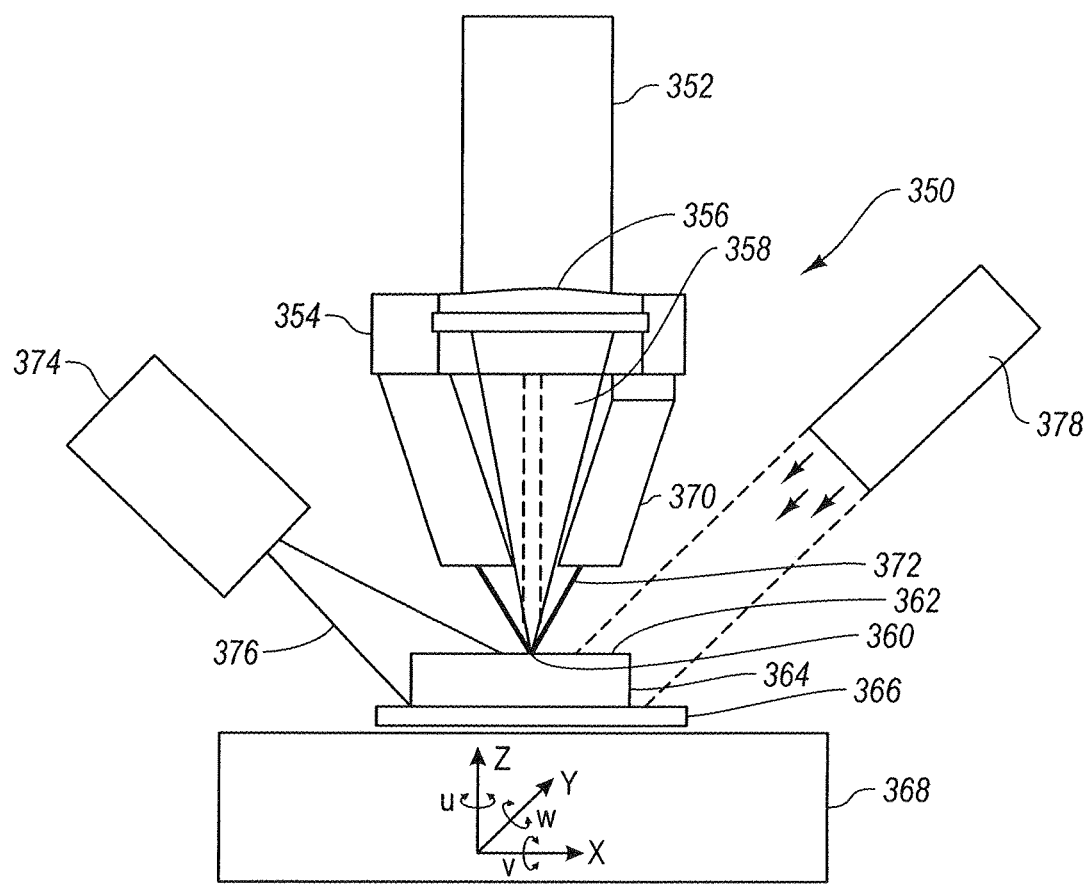
FIG. 8 is a schematic diagram that illustrates an embodiment of a stream-cutting apparatus.

FIG. 8 illustrates an embodiment of a stream-cutting assembly 350. The stream-cutting assembly 350 can be at least part of the stream-cutting apparatus 112 as illustrated in FIG. 4, and/or or the shaping system 230 of FIG. 7. Accordingly, the stream-cutting assembly 350 can include a stream supply 352, wherein at least a portion of the stream supply 352 is enclosed within a housing 354. The stream supply 352 can be configured to generate and/or supply a stream of energy. Alternatively, the stream supply 352 can be configured to store and/or supply a stream of matter.

Additionally, the housing can optionally include an aiming apparatus 356. As such, the stream supply 352 can be configured to supply a stream of energy and/or a stream of matter to be directed through the aiming apparatus 356, which acts to aim or further direct the stream of energy or stream of matter towards a green body 364. As such, the aiming apparatus 356 can create an aimed stream 358 with a trajectory aimed at a cutting site 360 on the green body 364 so that a stream-cut surface 362 is formed thereon.

In one embodiment, in order to enable precise three-dimensional cutting and shaping, the green body 364 can be retained on a turret 366 to rotate the green body 364. Additionally, the stream-cutting assembly 350 can include a mechanical feature 368 that is configured to move the green body 364 in various three-dimensional movements and/or rotations so that the focused stream 358 can strike the green body 364 at various cutting sites 360. The mechanical feature 368 along with the turret 366 can move the green body 364 in the x, y, and z axes and rotate with a rotation "u" around the z-axis, a rotation "w" around the y-axis, and rotation "v" around the x-axis. This enables a precise and intricate structure to be cut into the green body 364 within the stream-cutting assembly 350. Alternatively, the stream-cutting assembly can move the stream relative to a stationary green body 364, as described in more detail below.

Accordingly, the mechanical feature 386 can move and/or rotate the green body 364 by being outfitted with rubberized or other malleable endpoints that contact the green body 364 so as to not deform the green body 364. As such, these malleable endpoints can provide favorable interactions with the green body 364 so as to not deform, dent, crack, or otherwise stress or fatigue the green body 364 during the stream-cutting process.

In another embodiment, the housing 354 of the stream-cutting assembly 350 can include a coaxial gas assist device 370. Such a coaxial gas assist device 370 can be configured to emit an assist gas 372 during the stream-cutting procedure. An assist gas is a flow of air, other type of gas, concurrent with, and often peripheral to, the stream of energy or stream of matter. Alternatively, a flow of a liquid (e.g., assist fluid), such as water, can be used in place of an assist gas. A significant feature of gas-assisted stream-cutting is that the material being cut from the body is ejected or removed by the force of the gas jet coaxial to the stream of energy or stream of matter to produce relatively smooth stream-cut surfaces. Some examples of the different types of gases that can be used in gas-assisted cutting include oxygen, nitrogen, argon, and the like. Preferably, the gas is delivered at a pressure up to about 15 bars. Additional information about coaxial assist gas 372 will be described below.

In another embodiment, the stream-cutting assembly 350 can include a scanner 374. Similar to the three-dimensional virtual image generator 114 of FIG. 4, and/or the scanning system 230 of FIG. 7, a scanner 374 can be implemented into the stream-cutting assembly 350. The scanner 374 can be used to continuously or intermittently scan the surface of the green body 364. Accordingly, the scanner 374 emits a scanning beam 376 toward the green body 364, and more specifically toward any stream-cut surface 362. This can monitor the cutting sites 360 as well as the stream-cut surfaces 362. By including a scanner 374 in the stream-cutting assembly 350, the cutting and shaping can be monitored so as to ensure that the features formed thereon are in accordance, or substantially similar, with the three-dimensional virtual image. The scanning beam 376 and scanner 374 can be a part of a means of scanning three-dimensional images, as is well known in the art.

In another embodiment, the stream-cutting assembly 350 includes a power blower 378. While the stream-cutting assembly 350 can include a coaxial gas device 370 in order to emit a coaxial assist gas 372, such coaxial gas 372 may be insufficient for removing large pieces of green material cut from the bulk green body 364. Accordingly, a power blower 378 can be used in order to forcefully blow air, gas, or other fluid across the green body 364 so as to remove any particulates or large pieces of material. Alternatively, the power blower 378 can be configured as a vacuum. Similar to the power blower 387, a vacuum can also be used in order to remove the particulates or large pieces of material cut away from the green body 364. Thus, the power blower 378 can be used intermittently during the stream-cutting protocol.

In another embodiment, along with the coaxial gas device 372, the power blower 378 can blow a cooling air or fluid so as to cool the green body 364. This can be used to remove unwanted heat from the green body 364 or to prevent undesired melting of the binder or sinterable particles.

Figure 9A:
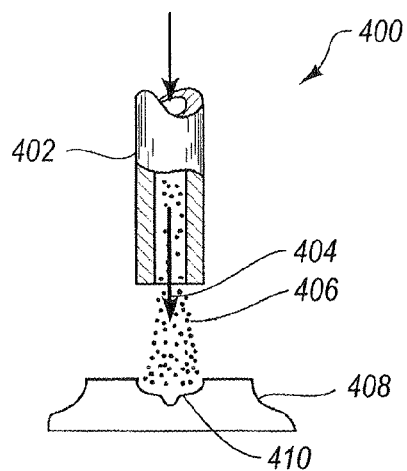
FIG. 9A is a schematic diagram that illustrates an embodiment of a stream-cutting nozzle.
Figure 9B:
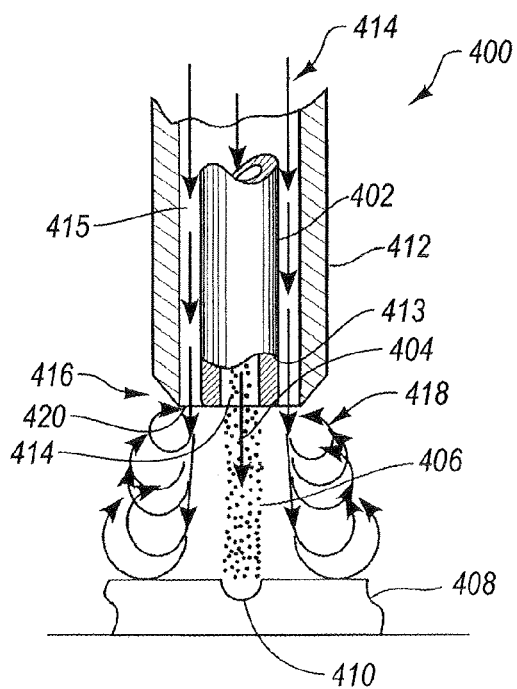
FIG. 9B is a schematic diagram that illustrates an embodiment of a coaxial stream-cutting nozzle.
Figure 9C:
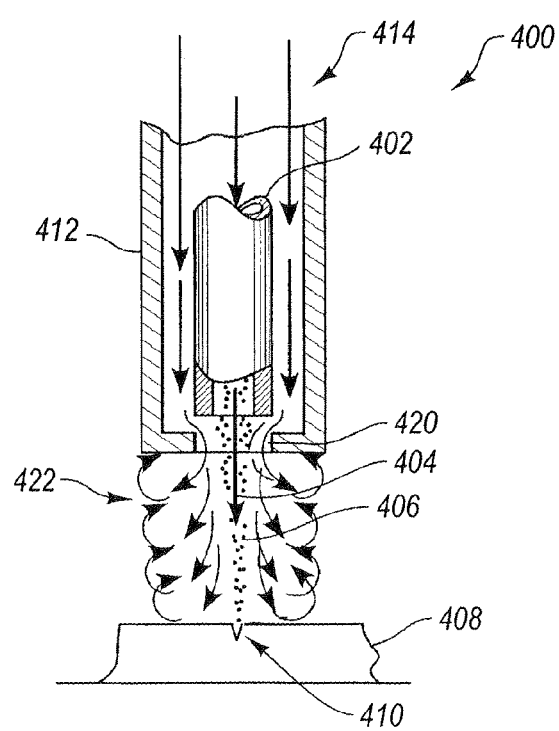
FIG. 9C is a schematic diagram that illustrates an embodiment of a coaxial stream-cutting nozzle.

With reference now to FIGS. 9A, 9, and 9C various features and elements of an aiming apparatus 400 are now illustrated and described. Such an aiming apparatus 400 can be used with the shaping system 230 of FIG. 7 as well as the stream-cutting assembly of FIG. 8.

In any event, the aiming apparatus 400 includes a nozzle 402 that is configured to emit a stream of energy 404, as represented by the arrow being directed therethrough. Additionally, the nozzle 402 can be configured to emit a stream of matter 406, as represented by the plurality of dots flowing through the nozzle 402. Accordingly, the nozzle 402 can be configured to aim the stream of energy 404 and/or the stream of matter 406 toward a cutting surface 410 on the green body 408. Thus, by aiming the nozzle 402, precise and intricate shapes can be formed.

With particular reference to FIG. 9B, the aiming apparatus 400 includes an inner nozzle 402a that is encased within the lumen of an outer nozzle 402b, which together forms a coaxial nozzle 412. Such a coaxial nozzle 412 includes an inner chamber 413 to aim the stream of energy 404 and/or the stream of matter 406. Additionally, the coaxial nozzle 412 includes an outer or coaxial chamber 415, wherein the outer or coaxial chamber 415 directs a flow of assist gas 414.

As depicted in FIG. 9B, the coaxial nozzle 412 includes a coaxial nozzle opening 416. The coaxial nozzle opening 416 includes a first opening 419 for the stream of energy 404 and/or the stream of matter 406 that is separate and independent from the second opening 421 that provides the assist gas 414. In this configuration, the coaxial nozzle opening 416 produces coaxial eddies 418 of the assist gas 414 in a manner that removes and blows away the cut particulates or materials.

With specific reference now to FIG. 9C, another embodiment of a coaxial nozzle 402 is illustrated. As such, the coaxial nozzle 402 can include a combining aperture 420. Such a combining aperture 420 includes a single opening for the stream of energy 404 and/or matter 406 as well as the assist gas 414. The combining aperture 420 can also produce eddies 422 to remove particles or matter from the green body 408.

In any event, various configurations of stream nozzles 402 can be provided to produce a precisely cut green body 408 in accordance with a virtual image or other desired shape. As such, this can include providing streams of energy 404 and/or matter 406 along with the assist gas 414 in a manner that enhances the stream-cutting protocol.

Figure 10:
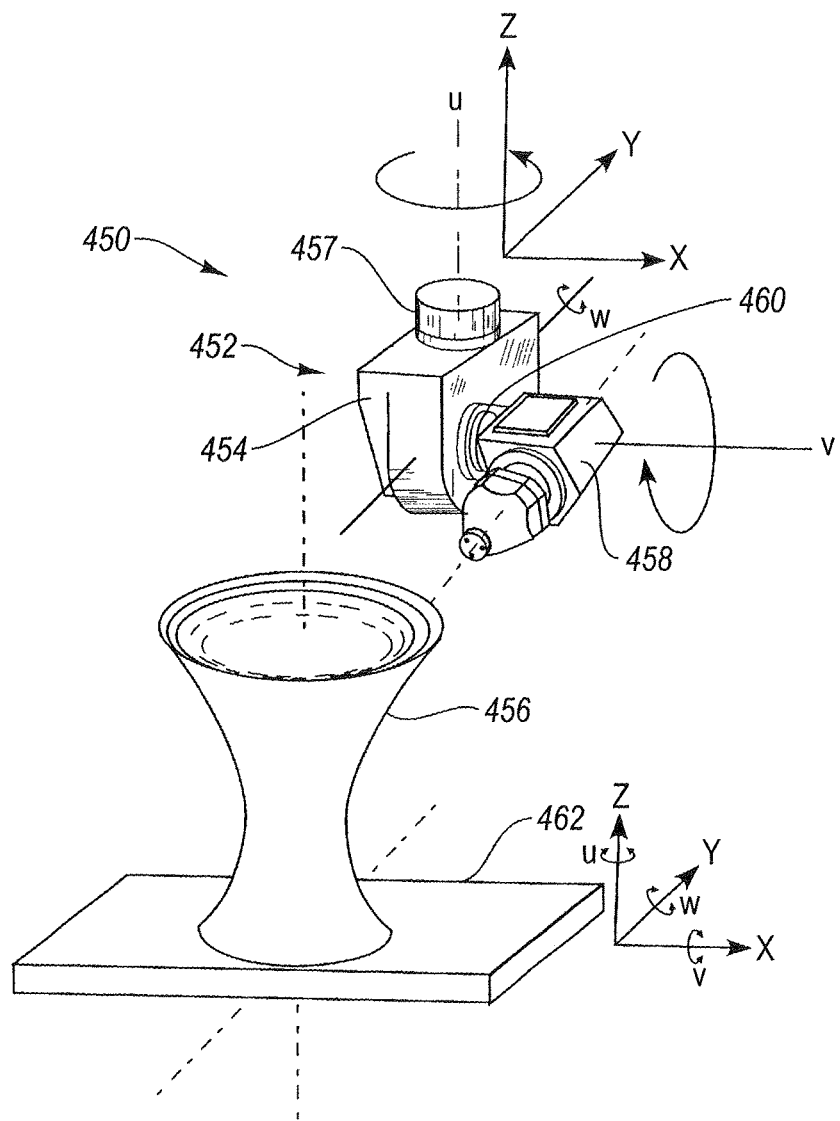
FIG. 10 is a schematic diagram that illustrates an embodiment of a three-dimensional stream-cutting system.

With reference now to FIG. 10, an embodiment of a three-dimensional cutting system 450 is illustrated and described. Such a three-dimensional cutting system 450 can be implemented in the stream-cutting apparatus of 112 of FIG. 4 as well as in any other stream-cutting system or process described herein. Accordingly, the three-dimensional cutting system 450 includes a three-dimensional cutting device 452 that is configured to move in the three-axes of movement. As such, the cutting device 452 can move longitudinally in the z-axis, x-axis, and y-axis as well as rotate in around each axis. This enables the cutting device 452 to move about and around a green body 456 being cut.

In the illustrated embodiment, the cutting device 452 includes first body 454 attached to a swivel coupling 457 that is configured such that it can rotate the first body 454 with a rotation "u" around the z-axis. The swivel coupling 457 couples the first body 454 with additional robotics (not shown) that enable movement in various degrees of freedom. More particularly, another swivel coupling (not shown) is included within the robotics that can enable a rotation "w" around the y-axis. These rotations enable the first body 452 to be moved around the green body 456.

The cutting device 452 can also include a cutting nozzle 458 which is coupled with the first body 454 by a swivel coupling 460. As such, the cutting nozzle 458 can also move in the x, y, and z-axes along with the first body 454. Additionally, the swivel coupling 460 allows for the cutting nozzle 458 to be capable of rotating with a rotation "v" about the x-axis. By being capable of additionally rotating with the "v" rotation, the three-dimensional cutting device 452 is able to cut the green body 456 with precise and intricate details in order to provide various shapes.

In another embodiment, the three-dimensional cutting system 450 includes a mechanical feature 462, which can be substantially similar to the mechanical feature 386 of FIG. 8. Briefly, the mechanical feature 462 is configured to move the green body 456 relative to the cutting device 452. As such, the mechanical feature 458 can move in the x, y, and z-axes, and also rotate with rotations "u," "v" and "w". Thus, the mechanical feature 462 can move independently of and/or in cooperation with the cutting nozzle 458, which can enable enhanced cutting techniques.

In one embodiment, any of the stream-cutting equipment, systems, and/or processes can be configured to be operated and controlled by a computer and associated software. As such, the computer uses controlling software that receives input data from a three-dimensional image of the shape to be cut into the green body. The controlling software can obtain the input data from images that have been generated or modified with CAD software. Accordingly, any image that is stored within a computer memory, such as the data storage device 234 illustrated in FIG. 7, can be used and controlled by the stream-cutting apparatus in order to create a three-dimensional structure from the green body material.

In one embodiment, the process or method of shaping a green body can include cutting a first portion of the green body intermediate away from a second portion with a stream of energy or a stream of matter such as with a laser, electron beam, or water-jet, so as to form a stream-cut surface such as a laser-cut surface, electron beam-cut surface, or a water-jet surface on the resulting shaped green body. This can either form a substantially smooth surface or an uneven surface.

In one embodiment, a process or method of stream-cutting a green body can be conducted in a vacuum or under low pressure. Also, the surface being stream-cut can be facing in a downward direction (inverted) so that any material ejected from the surface can fall away from the surface. When stream-cutting is performed on an inverted surface, the green body can be rotated so that each site being cut can have the removed green body materials fall free and clear of the stream-cut surface. This can allow for the ejected particles and/or binder to escape the surface without being redeposited adjacent to the feature being formed by the ejected material. This can be especially favorable when the stream-cutting procedure generates heat and melts the binder at the site being cut because the melted binder can re-solidify after re-depositing, which can produce irregular features. Thus, the process of stream-cutting a green body can be performed so that smooth surfaces and rounded features are formed in the external surface without any re-deposited materials forming irregular features adjacent to, or on, the stream-cut surface.

While various features and embodiments of stream-cutting equipment, systems and processes have been discussed in connection with the present invention various modifications can be made thereto and still retain the inventive concept. As such, various other streams of energy or streams of matter may be used in order to cut the green body materials so as to provide the desired shape. Additionally, the stream-cutting equipment, systems and processes can be modified and changed, and still use streams of energy or streams of matter to shape a green body intermediate.

IX. Sintering Green Bodies

A method of making a sintered body is in accordance with the present invention in order to provide a sintered article prepared from a shaped green body. Briefly, the sintered body can be obtained from a green body that was prepared by molding a mixture of sinterable particles and binder into the shape of a green body intermediate. After the green body intermediate has been formed in the mold, the process includes shaping with a stream of energy and/or matter in order to obtain a green body having a desired shape. The shaped green body can then be sintered in order to yield a sintered article having the desired shape. The sintering can be performed in a sintering apparatus 126 as depicted in FIG. 5. In any event, sintering a shaped green body can result in an article of manufacture that is either ready for use, or requires additional processing or finishing.

In one embodiment, a de-binding process can be carried out to remove the binder prior to sintering the shaped green body. As such, the de-binding can be performed by heat treatment in an oxidizing or non-oxidizing atmosphere, for instance, under a vacuum or low pressure. For example, the de-binding can be performed at about $1 \times 10^{-1}$ Torr (13.3 Pa) to about $1 \times 10^{-6}$ Torr ($1.3 \times 10^{-4}$ Pa). Alternatively, the de-binding can be performed at a higher pressure such as $1 \times 10^{-1}$ Torr (13.3 Pa) to about $1 \times 10^{3}$ Torr ($1.3 \times 10^{5}$ Pa) or above $1 \times 10^{3}$ Torr in nitrogen, argon, or other inert gas. Also, the de-binding temperature can be within the range of about 80° C. to about 750° C., more preferably about 100° C. to about 600° C., and most preferably about 150° C. to about 450° C. In any event, the de-binding can occur by melting, evaporating, or decomposing the binder.

In one embodiment, the sintering process can be performed in an oxidizing or an inert gas at a low pressure from about $1 \times 10^{-1}$ Torr (13.3 Pa) to about $1 \times 10^{-6}$ Torr ($1.3 \times 10^{-4}$ Pa) at an elevated temperature. Alternatively, the sintering can be performed at a higher pressure such as $1 \times 10^{-1}$ Torr (13.3 Pa) to about $1 \times 10^{3}$ Torr ($1.3 \times 10^{5}$ Pa) or above $1 \times 10^{3}$ Torr at an elevated temperature. As such, the binder can be substantially removed during the sintering process. Alternatively, the sintering process can remove a substantial amount, but not all of the binder, wherein some of the binder can remain depending on the binding system. The sintering temperature can range from about 750° C. to about 2,500° C., more preferably about 900° C. to about 2,000° C., and most preferably 1000° C. to about 1500° C.

Additionally, the sintering times can range from about 0.5 hours to about 15 hours, more preferably about 1 hour to about 10 hours, and most preferably about 2 hours to about 8 hours. Sometimes, however, sintering can last up to about 24 hours. Additionally, the sintering process should be modulated in order to grow the sinterable powder grains into a dense sintered body. Accordingly, the sintered body should have a high density with a low porosity compared to the green body.

When the green body is sintered, the volume shrinks as the porosity decreases and the density increases. This can happen as the majority of the binder is melting and/or evaporating so as to draw the individual sinterable particles closer together. As such, the green body can be fabricated and shaped to be larger than the resultant sintered article in order to accommodate for the volume lost during sintering. The volume decrease between the size of a green body and the size of a sintered article can range from about 10% to about 35%, more preferably about 12% to about 30%, and most preferably about 15% to about 25%; however, a typical volume decrease can be about 20%.

Since the volume of the green body will gradually decrease during sintering, the various features carved into the shaped green body can be fabricated so as to take shrinkage into account. This can allow for the stream-cut features to be cut with a margin of error, or to cut larger features than will be present after the sintering process. Thus, when the green body is stream-cut, the intricate shaping can result in even more precise and intricate features after sintering.

Another result of the shrinkage can include the topology of the sintered body becoming smoother when compared to the green body prior to sintering. More particularly, when irregular features are formed during stream-cutting, these features can be smoothed out during sintering. On the other hand, this smoothing effect does not necessarily have to remove any of the rough features, but can create a better surface with less obtuse or sharp edges.

In one embodiment, the sintering or de-binding process can remove impurities or unfavorable deposits from the surface of the sintered body. When the green body is cut with a stream of energy, such as a laser, electron beam, ion beam and the like, that generates heat in order to melt and/or vaporize the binder before being sintered, the heat-cut surface on the sintered body can be substantially devoid of being charred after the sintering process. For example, when a sintered piece is laser-cut, these laser-cut surfaces tend to be charred and blackened and require additional processing or finishing in order to remove the charred or blackened material. Charred bodies can present unfavorable characteristics for many applications.

Accordingly, the sintering process and/or the de-binding process can function to partially or substantially de-char the particles, and hence the sintered body can be substantially devoid of being charred or blackened at the heat-cut surfaces. Without being bound to any particular theory, it is thought that when the binder melts or is otherwise removed from the green body, the binder draws the charred material away from the green body. This can occur during the sintering or de-binding process because a portion of the binder will melt and flow over the heat-cut surface and leech the charred material away from the particles. Thus, when a green body is cut with a heat generating stream of energy, the heat-cut surfaces can similarly have charred surfaces; however, the heat-cut surface can be less charred after being sintered compared to the same heat-cut surface on the green body prior to being sintered.

Also, without being bound to any particular theory, it is thought that an oxidized layer forms over the exterior surface of the green body as it is being sintered, especially when in an oxidizing atmosphere. Accordingly, shaping the green body with a stream of energy or matter prior to sintering can allow for the oxidized layer to form on the stream-cut surface during sintering. The oxidized layer is thought to impart favorable characteristics such as corrosion resistance, biocompatibility, and the like. On the other hand, cutting a sintered article can destroy the oxidized surface layer, and decrease or inhibit these favorable characteristics. Thus, at least one stream-cut surface on the sintered body can have a topology characterized by an oxidized surface formed by sintering, wherein the sintering is conducted after the green body has been cut and shaped as described herein.

Additionally, the sintered body can be further processed after sintering such as grinding, sanding, or the like to provide enhanced surface characteristics. Thus, at least one stream-cut surface on the exterior surface of the sintered body can have a smoother topology compared to at least one stream-cut surface on the exterior surface of the shaped green body.

The present invention may be embodied in other specific forms without departing from its spirit or essential characteristics. The described embodiments are to be considered in all respect only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing an orthodontic bracket or an orthodontic base plate, comprising:
   molding a mixture of sinterable particles and organic binder into a green body in the shape of the orthodontic bracket or the orthodontic base plate;
   removing sinterable particles from the green body using a stream of energy to yield at least one thermal-cut surface of the green body including at least one melted surface layer and a plurality of protrusions, recesses, and undercuts that define an irregular and uneven surface on the green body;
   removing the organic binder prior to sintering the green body; and
   sintering the green body to form the orthodontic bracket or the orthodontic base plate.

2. The method of claim 1, wherein the thermal-cut surface forms at least a portion of a surface configured to attach the orthodontic bracket or the orthodontic base plate to a tooth.

3. The method of claim 1, wherein removing sinterable particles further includes vaporizing, melting, and/or burning the organic binder associated with the removed sinterable particles, and removing the organic binder prior to sintering the green body includes removing the organic binder remaining after the organic binder associated with the removed sinterable particles is vaporized, melted, and/or burned.

4. A method of manufacturing an orthodontic bracket or an orthodontic base plate, comprising:
   molding a mixture of sinterable particles and organic binder into a desired shape of a green body;
   removing sinterable particles from the green body using a stream of energy to yield a thermal-cut portion of the green body that includes at least one melted surface layer and a plurality of protrusions, recesses, and undercuts that define an irregular and uneven surface on the green body;
   removing the organic binder prior to sintering the green body; and
   sintering the green body to form the orthodontic bracket or the orthodontic base plate.

5. The method of claim 4, wherein the irregular and uneven surface forms at least a portion of a surface configured to attach the orthodontic bracket or the orthodontic base plate to a tooth.

6. A green body for use in making an orthodontic appliance comprising:
   a body of sinterable particles mixed with a binder in the shape of the orthodontic appliance, the body including at least one thermal-cut surface that includes at least one melted surface layer and a plurality of protrusions, recesses, and undercuts that define an irregular and uneven surface on the green body.

7. The green body of claim 6, wherein the body corresponds to a shape of an orthodontic bracket and the thermal-cut surface defines a bonding surface for bonding the orthodontic bracket to a tooth following sintering of the body.

8. The green body of claim 6, wherein the melted surface layer includes a portion of metal particles melted together.

9. The green body of claim 6, wherein the thermal-cut surface includes sinterable particles that are held together by melted binder.

10. The green body of claim 6, wherein the thermal-cut surface includes a charred or blackened layer.

11. The green body of claim 6, wherein the sinterable particles include one of metallic particles and ceramic particles.

12. The green body of claim 11, wherein the metallic particles are selected from the group consisting of aluminum, nickel, titanium, copper, cobalt, and stainless steel.

13. The green body of claim 6, wherein the plurality of protrusions, recesses, and undercuts of the thermal-cut surface includes a plurality of macro-protrusions, macro-recesses, and macro-undercuts and that further includes a plurality of micro-protrusions, micro-recesses, or micro-undercuts superimposed on the macro-protrusions, macro-recesses, or macro-undercuts.

* * * * *